US007794723B2

(12) United States Patent
Gaudernack et al.

(10) Patent No.: US 7,794,723 B2
(45) Date of Patent: Sep. 14, 2010

(54) ANTIGENIC PEPTIDES DERIVED FROM TELOMERASE

(75) Inventors: Gustav Gaudernack, Oslo (NO); Jon Amund Eriksen, Porsgrunn (NO); Mona Møller, Porsgrunn (NO); Marianne Klemp Gjertsen, Oslo (NO); Ingvil Sæterdal, Oslo (NO); Stein Sæbøe-Larsen, Oslo (NO)

(73) Assignee: GemVax AS, Oslo (NO)

( * ) Notice: Subject to any disclaimer, the term of this patent is extended or adjusted under 35 U.S.C. 154(b) by 33 days.

(21) Appl. No.: 11/332,378

(22) Filed: Jan. 17, 2006

(65) Prior Publication Data

US 2006/0106196 A1   May 18, 2006

Related U.S. Application Data

(62) Division of application No. 09/743,281, filed as application No. PCT/NO99/00220 on Jun. 30, 1999, now Pat. No. 7,030,211.

(30) Foreign Application Priority Data

Jul. 8, 1998 (NO) .................................. 19983141

(51) Int. Cl.
| | |
|---|---|
| A61K 31/00 | (2006.01) |
| A61K 38/00 | (2006.01) |
| A61K 38/16 | (2006.01) |
| A61K 38/28 | (2006.01) |
| A61K 39/00 | (2006.01) |
| A61K 39/38 | (2006.01) |
| G01N 33/00 | (2006.01) |
| G01N 33/48 | (2006.01) |
| A01N 37/18 | (2006.01) |
| A01N 61/00 | (2006.01) |

(52) U.S. Cl. .................... 424/185.1; 424/184.1; 436/64; 436/86; 514/1; 514/2; 514/4; 514/8; 514/13

(58) Field of Classification Search .............. 424/184.1, 424/185.1; 436/64, 86; 514/1, 2, 4, 8, 13
See application file for complete search history.

(56) References Cited

U.S. PATENT DOCUMENTS 5,968,506 A   10/1999   Weinrich et al. ............ 424/94.5
6,166,178 A   12/2000   Cech et al. .................. 530/324

FOREIGN PATENT DOCUMENTS

| JP | 10-504284 | 4/1998 |
|---|---|---|
| WO | 92/14756 | 9/1992 |
| WO | WO 95/34638 | 12/1995 |
| WO | WO 97/28818 | 8/1997 |
| WO | 97/35619 | 10/1997 |
| WO | 98/01542 | 1/1998 |
| WO | 98/14593 | 4/1998 |
| WO | WO 98/21343 | 5/1998 |
| WO | 99/50386 | 10/1999 |
| WO | 99/50392 | 10/1999 |

OTHER PUBLICATIONS

Chamberlain and Kaufman. Innovations and strategies for the development of anticancer vaccines. Exp. Opin. Pharmacother. 1(4): 603-614, 2000.*
Amino acid sequence alignment between Applicants' SEQ ID No. 2 and U.S. Patent 6,166,178 (filed Nov. 19, 1997).*
Bodey et al. Failure of Cancer Vaccines: The significant limitations of this Approach to Immunotherapy. Anticancer Research 70: 2665-2676, 2000.*
Gura. Systems for Identifying New Drugs are Often Faulty. Science 278: 1041 and 1042, Nov. 7, 1997.*
Esteban Cells et al., "Epitope Selection and Development of Peptide Based Vaccines to Treat Cancer," Cancer Biology, vol. 6: 329-336 (1995).
Ettore Appella et al., "Synthetic Antigenic Peptides as a New Strategy for Immunotherapy of Cancer," Biomedical Peptides, Proteins & Nucleic Acids, vol. 1: 177-184 (1995).
Esteban Cells et al., "Identification of Potential CTL Epitopes of Tumor-Associated Antigen Mage-1 for Five Common HLA-A Alleles," Molecular Immunology, vol. 31(18): 1423-1430 (1994).
Ichiro Kawashima et al., "The Multi-Epitope Approach for Immunotherapy for Cancer: Identification of Several CTL Epitopes from Various Tumor-Associated Antigens Expressed on Solid Epithelial Tumors," Human Immunology, vol. 59: 1-14 (1998).
Jörg Ruppert et al., "Prominent Role of Secondary Anchor Residues in Peptide Binding to HLA-A2.1 Molecules," Cell, vol. 74: 929-937 (Sep. 10, 1993).
Ruppert et al. "Identification of Peptides Having HLA-A2.1 Binding Motif in Telomerase Protein," (1993).
Howard M. Grey et al., "Class I MHC-Peptide Interactions: Structural Requirements and Functional Implications," Cancer Surveys, vol. 22: 37-49 (1995).
Declaration by Anish Majumidar (Feb. 8, 2006).
Boris Minev et al., "Cytotoxic T Cell Immunity against Telomerase Reverse Transcriptase in Humans," PNAS, vol. 97(9): 4796-4801 (Apr. 25, 2000).
Gamal H. Eltabbakh, MD, "Telomerase in Gynecologic Cancers," Obstetrics and Gynecology, vol. 90(6): 1015-1019 (Dec. 1997).

(Continued)

*Primary Examiner*—Alana M. Harris
(74) *Attorney, Agent, or Firm*—Fitzpatrick, Cella, Harper & Scinto

(57) ABSTRACT

This invention relates to proteins or peptides that elicit T cell mediated immunity, and to cancer vaccines and compositions for anti-cancer treatment comprising such proteins or peptide fragments. This invention also relates to pharmaceutical compositions comprising the proteins or peptides and methods for generating T lymphocytes capable of recognizing and destroying tumor cells in a mammal. More specifically, a telomerase protein or peptide for use in a method of treatment or prophylaxis of cancer is provided. In a preferred embodiment, the method comprises generating a T cell response against telomerase.

8 Claims, 4 Drawing Sheets

OTHER PUBLICATIONS

David-Alexandre Gross et al., "High Vaccination Efficiency of Low-Affinity Epitopes in Antitumor Immunotherapy," J. of Clinical Investigation, vol. 113(3): 425-433 (Feb. 2004).

Ricardo Cibotti et al., "Tolerance to a Self-Protein Involves its Immunodominant but does not Involve Its Subdominant Determinants," Proc. Natl. Acad. Sci. USA, vol. 89: 416-420 (Jan. 1992).

HLA Peptide Motif Search Results Ranking Potential 9-mer Peptides Based on Predicted Half-time Dissociation to HLA Class I Molecule A_0201 Using the Algorithm available at http://bimas.dcrt.nih.gov/cgi-bin/molbio/ken_parker_comboform, printed Dec. 19, 2000, pp. 1-2.

Facsimile letter dated Feb. 14, 2005 from Rubab Khan, Editorial Assistant, Cell Metabolism, Immunity, Current Biology to Michael Schiff of Geron Corporation.

HLA Peptide Binding Predictions homepage, available at http://bimas.dcrt.nih.gov/cgi-bin/molbio/ken_parker_comboform.

Information & Background on the HLA Peptide Motif Searches, pp. 1-5, available at http://thr.cit.nih.gov/molbio/hla_bind/hla_motif_search_info.html.

HLA Peptide Motif Search Results Ranking Potential 9-mer Peptides Based on Predicted Half-time Dissociation to Various HLA Class I Molecules Using the Algorithm available at http://bimas.dcrt.nih.gov/cgi-bin/molbio/ken_parker_comboform, printed Dec. 14, 2004, pp. 1-20.

Robert H. Vonderheide, et al., "The Telomerase Catalytic Subunit Is a Widely Expressed Tumor-Associated Antigen Recognized by Cytotoxic T Lymphocytes," Immunity, vol. 10, Jun. 1999, pp. 673-679.

HLA Peptide Search Results Ranking Potential 9-mer Peptides Based on a Predicted Half-time Dissociation to HLA Class I Molecule A_1101 Using the Algorithm available at http://bimas.dcrt.nih.gov/cgi-bin/molbio/ken_parker_combofrom, printed May 7, 2004.

HLA Peptide Search Results Ranking Potential 9-mer Peptides Based on a Predicted Half-time Dissociation to HLA Class I Molecule A3 Using the Algorithm available at http://bimas.dcrt.nih.gov/cgi-bin/molbio/ken_parker_combofrom, printed May 7, 2004.

HLA Peptide Search Results Ranking Potential 9-mer Peptides Based on a Predicted Half-time Dissociation to HLA Class I Molecule A_0201 Using the Algorithm available at http://bimas.dcrt.nih.gov/cgi-bin/molbio/ken_parker_combofrom, printed May 7, 2004.

HLA Peptide Search Results Ranking Potential 9-mer Peptides Based on a Predicted Half-time Dissociation to HLA Class I Molecule A1 Using the Algorithm available at http://bimas.dcrt.nih.gov/cgi-bin/molbio/ken_parker_combofrom printed May 7, 2004.

HLA Peptide Search Results Ranking Potential 9-mer Peptides Based on a Predicted Half-time Dissociation to HLA Class I Molecule A24 Using the Algorithm available at http://bimas.dert.nih.gov/cgi-bin/molbio/ken-parker-comboform printed May 7, 2004.

Kenneth C. Parker, et al., "Sequence Motifs Important for Peptide Binding to the Human MHC Class I Molecule, HLA-A2," J. Immunol., vol. 149, No. 11, Dec. 1992, pp. 3580-3587.

Kenneth C. Parker, et al., "Scheme for Ranking Potential HLA-A2 Binding Peptides Based on Independent Binding of Individual Peptide Side-Chains," J. Immunol., vol. 152, No. 1, Jan. 1994, pp. 163-175.

Toru M. Nakamura, et al., "Telomerase Catalytic Subunit Homologs from Fission Yeast and Human," Science, vol. 277, Aug. 15, 1997, pp. 955-959.

Miles P. Davenport, et al., "An Empirical Method for the Predication of T-Cell Epitopes," Immunogenetics, vol. 42, No. 5, 1995, pp. 392-397.

Gabriel E. Meister, et al., "Two Novel T Cell Epitope Prediction Algorithms Based on MHC-Binding Motifs; Comparison of Predicted and Published Epitopes from *Mycobacterium Tuberculosis* and HIV Protein Sequences," Vaccine, vol. 13, No. 6, 1995, pp. 581-591.

Juergen Hammer, et al., "HLA Class II Peptide Binding Specificity and Autoimmunity," Advances in Immunology, vol. 66, 1997, pp. 67-100.

Fax Memo dated Aug. 2, 2004 from the British Library to Will Arends of Lloyd Wise.

Smita K. Nair, et al., "Induction of Cytotoxic T Cell Responses and Tumor Immunity Against Unrelated Tumors Using Telomerase Reverse Transcriptase RNA Transfected Dendritic Cells," Nature Medicine, vol. 6, No. 8, Sep. 2004, pp. 1011-1017.

Motomi Mori, et al., "HLA Gene and Haplotype Frequencies in the North American Population: The National Marrow Donor Program Donor Registry," Transplantation, vol. 64, No. 7, Oct. 1997, pp. 1017-1027.

Axelrod, N., "Of telomeres and tumors," Nature Medicine, vol. 2, No. 2, pp. 158-159, 1996.

Soria, J-C., et al., "Téloméres, télomérase et cancer," Bull. Cancer, vol. 84, No. 10, pp. 963-970, 1997. (Abstract in English).

Nijman et al., "P53 a Potential Target for Tumor-directed T Cells," Immunology Letters 40: 171-178, 1993.

Meyerson, M., et al., "hEST2, the Putative Human Telomerase Catalytic Subunit Gene, Is Up-Regulated in Tumor Cells and During Immortalization," Cell, vol. 90, pp. 785-795, 1997.

GenCore database sequence alignment between Applicants' SEQ ID No. 2 and U.S. Patent No. 6,166,178 sequence 31.

Huminiecki, L., "Telomerase as a therapeutic target," Acta Biochimica Polonica, vol. 43, No. 3, pp. 531-538, 1996.

Harrington, L., et al., "A Mammalian Telomerase-Associated Protein," Science, vol. 275, pp. 973-977, 1997.

Nakayama, J., et al., "*TLP1*: A Gene Encoding a Protein Component of Mammalian Telomerase Is a Novel Member of WD Repeats Family," Cell, vol. 88, pp. 875-884, 1997.

Gaudernack, G., "T cell responses against mutant *ras*: a basis for novel cancer vaccines," Immunotechnology, vol. 2, pp. 3-9, 1996.

Gjertsen, M.K., et al., "Ex Vivo ras Peptide Vaccination in Patients With Advanced Pancreatic Cancer: Results of a Phase I/II Study," Int. J. Cancer, vol. 65, pp. 450-453, 1996.

Gjertsen, M. K., et al., "Characterisation of immune responses in pancreatic carcinoma patients after mutant p21 ras peptide vaccination," British J. of Cancer, vol. 74, pp. 1828-1833, 1996.

Gjertsen, M. K., et al., "Cytotoxic $CD4^+$ and $CD8^+$ T Lymphocytes, Generated by Mutant p21-*ras* (12VAL) Peptide Vaccination of a Patient, . . . This Mutation," Int. J. Cancer, vol. 72, pp. 784-790, 1997.

Gjertsen, M. K., et al., "Mutated Ras Peptides as Vaccines in Immunotherapy of Cancer," Vox Sanguinis, vol. 74 (Suppl. 2), pp. 489-495, 1998.

Dahse, R., et al., "Telomeres and telomerase: biological and clinical importance," Clinical Chemistry, vol. 43, No. 5, pp. 708-714, 1997.

Deres, K., et al., "In vivo priming of virus-specific cytotoxic T lymphocytes with synthetic lipopeptide vaccine," Nature, vol. 342, No. 6249, pp. 561-564, 1989.

Tighe, H., et al., "Gene vaccination: plasmid DNA is more than just a blueprint," Immunology, Today, vol. 19, No. 2, pp. 89-97, 1998.

Rammensee, H-G., et al., "MHC ligands and peptide motifs: first listing," Immunogenetics, vol. 41, No. 4, pp. 178-228, 1995.

Barinaga, M., "Getting Some "Backbone": How MHC Binds Peptides," Science, vol. 257, pp. 880-881, 1992.

Grottier, C.W., et al., "Identification of a Specific Telomere Terminal Transferase Activity in Tetrahymena Extracts," Cell, vol. 43, pp. 405-413, 1985.

Collins, K., et al., "Purification of Tetrahymena Telomerase and Cloning of Genes Encoding the Two Protein Components of the Enzyme," Cell, vol. 81, pp. 677-686, 1995.

Harley, C.B., et al., "Telomerase, Cell Immortality, and Cancer," Cold Spring Harbor Symp. Quant. Biol., vol. 59, pp. 307-315, 1994.

Kim, N.W., et al., "Specific Association of Human Telomerase Activity with Immortal Cells and Cancer," Science, vol. 266, pp. 2011-2015, 1994.

Broccoli, D., et al., "Telomerase activity in normal and malignant hematopoietic cells," Proc. Natl. Acad. Sci. USA, vol. 92, No. 20, pp. 9082-9086, 1995.

Counter, C.M., et al., "Telomerase Activity in Normal Leukocytes and in Hematologic Malignancies," Blood, vol. 85, No. 9, pp. 2315-2320, 1995.

Hiyama, K., et al., "Activation of Telomerase in Human Lymphocytes and Hematopoietic Progenitor Cells," J. Immunology, vol. 155, No. 8, pp. 3711-3715, 1995.

Counter, C.M., et al., "Telomerase activity in human ovarian carcinoma," Proc. Natl. Acad. Sci. NAS USA, vol. 91, No. 8, pp. 2900-2904, 1994.

Shay, J.W., et al., "A Survey of Telomerase Activity in Human Cancer," Eur. J. Cancer, vol. 33, No. 5, pp. 787-791, 1997.

Klingelhutz, A.J. et al., "Telomerase activation by the E6 gene product of human papillomavirus type 16," Nature, vol. 380, No. 6569, pp. 79-82, 1996.

Sharma, S., et al., "Preclinical and clinical strategies for development of telomerase and telomere inhibitors," Annals of Oncology, vol. 8, No. 11, pp. 1063-1074, 1997.

Lurquin, C., et al., "Structure of the Gene of Tum⁻Transplantation Antigen P91A: The Mutated Exon Encodes a Peptide Recognized with $L^d$ by Cytolytic T Cells", Cell, vol. 58, pp. 293-303, 1989.

Calvin B. Harley, "Telomerase and cancer therapeutics," Nature Reviews 8: 167-179 (2008).

Kokhaei, P., et al., "Telomerase (hTERT 611-626) serves as a tumor antigen in B-cell chronic lymphocytic leukemia and generates spontaneously antileukemic, cytotoxic T cellls," Experimental Hematology 35: 297-304 (2007).

Bernhardt, S.L., et al., "Telomerase peptide vaccination of patients with non-resectable pancreatic cancer: a dose escalating phase I/II study," British Journal of Cancer 95: 1474-1482 (2006).

Brunsvig, P., et al., "Telomerase peptide vaccination: a phase I/II study in patients with non-small cell lung cancer," Cancer Immunol Immunother 55(12):1553-64 (2006).

Dahse, et al., "Telomeres and telomerase: Biological and clinical importance," Clinical Chemistry 43(5):708-714 (1997).

* cited by examiner

ANTIGENIC PEPTIDES DERIVED FROM TELOMERASE

This application is a divisional of U.S. patent application Ser. No. 09/743,281, filed Jul. 5, 2001, which is a 371 of PCT/NO99/00220, filed Jun. 30, 1999, the entire content of which is incorporated herein.

This invention relates to proteins or peptides that elicit T cell mediated immunity, and to cancer vaccines and compositions for anti-cancer treatment comprising such proteins or peptide fragments. This invention also relates to pharmaceutical compositions comprising the proteins or peptides and methods for generating T lymphocytes capable of recognizing and destroying tumor cells in a mammal.

Cancer develops through a multistep process involving several mutational events. These mutations result in altered expression/function of genes belonging to two categories: oncogenes and tumor suppressor genes. Oncogenes arise in nature from proto-oncogenes through point mutations or translocations, thereby resulting in a transformed state of the cell harboring the mutation. All oncogenes code for and function through a protein. Proto-oncogenes are normal genes of the cell that have the potential of becoming oncogenes. In the majority of cases, proto-oncogenes have been shown to be components of signal transduction pathways. Oncogenes act in a dominant fashion. Tumor-suppressor genes, on the other hand, act in a recessive fashion, i.e., through loss of function, and contribute to oncogenesis when both alleles encoding the functional protein have been altered to produce non-functional gene products.

The concerted action of a combination of altered oncogenes and tumor-suppressor genes results in cellular transformation and development of a malignant phenotype. Such cells are, however, prone to senescence and have a limited life-span. In the majority of cancers, immortalization of the tumor cells requires the turning on of an enzyme complex called telomerase. In somatic cells the catalytic subunit of this enzyme is normally not expressed. Additional events, such as the action of proteins encoded by a tumor virus or demethylation of silenced promoter sites, can result in expression of a functional telomerase complex in tumor cells.

In the field of human cancer immunology, the last two decades have seen intensive efforts to characterize genuine cancer specific antigens. In particular, effort has been devoted to the analysis of antibodies to human tumor antigens. The prior art suggests that such antibodies can be used for diagnostic and therapeutic purposes, for instance, in connection with an anti-cancer agent. However, antibodies can only bind to tumor antigens that are exposed on the surface of tumor cells. For this reason, the efforts to produce a cancer treatment based on the immune system of the body have been less successful than expected.

A fundamental feature of the immune system is that it can distinguish self from nonself and does not normally react against self molecules. It has been shown that rejection of tissues or organs grafted from other individuals is an immune response to the foreign antigens on the surface of the grafted cells. The immune response in general consists of a humeral response, mediated by antibodies, and a cellular response. Antibodies are produced and secreted by B lymphocytes and typically recognize free antigen in native conformation. They can therefore potentially recognize almost any site exposed on the antigen surface. In contrast to antibodies, T cells, which mediate the cellular arm of the immune response, recognize antigens only in the context of MHC molecules, and only after appropriate antigen processing. This antigen processing usually consists of proteolytic fragmentation of the protein, resulting in peptides that fit into the groove of the MHC molecules. This enables T cells to also recognize peptides derived from intracellular antigens.

T cells can recognize aberrant peptides derived from anywhere in the tumor cell, in the context of MHC molecules on the surface of the tumor cell. The T cells can subsequently be activated to eliminate the tumor cell harboring the aberrant peptide. In experimental models involving murine tumors it has been shown that point mutations in intracellular "self" proteins may give rise to tumor rejection antigens, consisting of peptides differing in a single amino acid from the normal peptide. The T cells recognizing these peptides in the context of the major histocompatibility (MHC) molecules on the surface of the tumor cells are capable of killing the tumor cells and thus rejecting the tumor from the host (Boon et al., 1989, Cell 58, 293-303).

MHC molecules in humans are normally referred to as HLA (human leucocyte associated antigen) molecules. There are two principal classes of HLA molecules, class I and class II. HLA class I molecules are encoded by HLA A, B and C subloci and primarily activate CD8+ cytotoxic T cells. HLA class II molecules, on the other hand, primarily activate CD4+ T cells and are encoded by the DR, DP and DQ subloci. Every individual normally has six different HLA class I molecules, usually two alleles from each of the three subgroups A, B and C, although in some cases the number of different HLA class I molecules is reduced due to the occurrence of the same HLA allele twice.

The HLA gene products are highly polymorphic. Different individuals express distinct HLA molecules that differ from those found in other individuals. This explains the difficulty of finding HLA matched organ donors in transplantations. The significance of the genetic variation of the HLA molecules in immunobiology is reflected by their role as immune-response genes. Through their peptide binding capacity, the presence or absence of certain HLA molecules governs the capacity of an individual to respond to specific peptide epitopes. As a consequence, HLA molecules determine resistance or susceptibility to disease.

T cells may inhibit the development and growth of cancer by a variety of mechanisms. Cytotoxic T cells, both HLA class I restricted CD8+ and HLA class II restricted CD4+, may directly kill tumor cells presenting the appropriate tumor antigens. Normally, CD4+ helper T cells are needed for cytotoxic CD8+ T cell responses, but if the peptide antigen is presented by an appropriate APC, cytotoxic CD8+ T cells can be activated directly, which results in a quicker, stronger and more efficient response.

While the peptides that are presented by HLA class II molecules are of varying length (12-25 amino acids), the peptides presented by HLA class I molecules must normally be exactly nine amino acid residues long in order to fit into the class I HLA binding groove. A longer peptide will result in non-binding if it cannot be processed internally by an APC or target cell, such as a cancer cell, before presenting in the class I HLA groove. Only a limited number of deviations from this requirement of nine amino acids has been reported, and in those cases the length of the presented peptide has been either eight or ten amino acid residues long.

Reviews of how MHC binds peptides can be found in Hans-Georg Rammensee, Thomas Friede and Stefan Stevanovic (1995, Immunogenetics 41, 178-228) and in Barinaga (1992, Science 257, 880-881). Male et al. (1987, *Advanced Immunology*, J.B. Lippincott Company, Philadelphia) offers a more comprehensive explanation of the technical background to this invention.

In our International Application PCT/NO92/00032 (published as WO92/14756), we described synthetic peptides and fragments of oncogene protein products that have a point of mutation or translocations as compared to their proto-oncogene or tumor suppressor gene protein. These peptides correspond to, completely cover or are fragments of the processed oncogene protein fragment or tumor suppressor gene fragment as presented by cancer cells or other antigen presenting cells and are presented as an HLA-peptide complex by at least one allele in every individual. These peptides were shown to induce specific T cell responses to the actual oncogene protein fragment produced by the cell by processing and presented in the HLA molecule. In particular, we described peptides derived from the p21-ras protein that had point mutations at particular amino acid positions, namely positions 12, 13 and 61. These peptides have been shown to be effective in regulating the growth of cancer cells in vitro. Furthermore, the peptides were shown to elicit CD4+ T cell immunity against cancer cells harboring the mutated p21-ras oncogene protein through the administration of such peptides in vaccination or cancer therapy schemes. Later we showed that these peptides also elicit CD8+ T cell immunity against cancer cells harboring the mutated p21-ras oncogene protein through the administration mentioned above (see M. K. Gjertsen et al., Int. J. Cancer, 1997, vol. 72, p. 784).

However, the peptides described above will be useful only in certain numbers of cancers, namely those that involve oncogenes with point mutations or translocation in a proto-oncogene or tumor suppressor gene. There is therefore a strong need for an anti-cancer treatment or vaccine that will be effective against a more general range of cancers.

In general, tumors are very heterogeneous with respect to genetic alterations found in the tumor cells. This implies that both the potential therapeutic effect and prophylactic strength of a cancer vaccine will increase with the number of targets against which the vaccine is able to elicit T cell immunity. A multiple target vaccine will also reduce the risk of new tumor formation by treatment escape variants from the primary tumor.

The enzyme telomerase has recently been the focus of attention for its supposed role in prevention of cellular aging. Telomerase is an RNA-dependent DNA polymerase, which synthesizes telomeric DNA repeats using an RNA template that exists as a subunit of the telomerase holoenzyme. The DNA repeats synthesized by the enzyme are incorporated into telomeres, which are specialized DNA-protein structures found at the ends of the linear DNA molecules which make up every chromosome. Telomerase was first identified in the ciliate *Tetrahymena* (Greider and Blackburn, 1985, *Cell* 43, 405-413). A human telomerase catalytic subunit sequence was recently identified by Meyerson et al. (1990, *Cell* 1197, 785-795) and Nakamura et al. (1997, *Science* 277, 955-959), who respectively named the gene hEST2 and hTRT. In addition, three other proteins that are associated with telomerase activity have also been identified: p80 and p95 of *Tetrahymena* (Collins et al., 1995, *Cell* 81, 677-686) and TP1/TLP1, which is the mammalian homologue of *Tetrahymena* p80 (Harrington et al., 1997, *Science* 275, 973-977; Nakayama et al., 1997, *Cell* 88, 875-884).

Telomerase is not expressed in most normal cells in the body. Most somatic lineages in humans show no detectable telomerase activity, but telomerase activity is detected in the germline and in some stem cell compartments, which are sites of active cell division (Harley et al., 1994, *Cold Spring Harbor Symp. Quant. Biol.* 59, 307-315; Kim et al., 1994, *Science* 266, 2011-2015; Broccoli et al., 1995, *PNAS USA* 92, 9082-9086; Counter et al., 1995, *Blood* 85, 2315-2320; Hiyama et al., 1995, *J. Immunol.* 155, 3711-3715). Telomeres of most types of human somatic cells shorten with increasing age of the organism, consistent with lack of telomerase activity in these cells. Cultured human cells also show telomere shortening. Telomere shortening continues in cultured human cells that have been transformed, until the telomeres have become critically short. At this point, termed the crisis point, significant levels of cell death and karyotypic instability are observed.

Immortal cells, which have acquired the ability to grow indefinitely in culture, emerge at rare frequency from crisis populations. These immortal cells have high levels of telomerase activity and stable telomeres. Telomerase activity is also readily detected in the great majority of human tumor samples analyzed to date (Kim et al., 1994, *Science* 266, 2011-2015), including ovarian carcinoma (Counter et al., 1994, *PNAS USA* 91, 2900-2904). A comprehensive review is provided by Shay and Bachetti (1997, *Eur. J. Cancer* 33, 787-791). Thus, activation of telomerase may overcome the barriers to continuous cell division imposed by telomere length. Cells that overcome the normal senescence mechanisms may do so by stabilizing telomere length, probably due to the activity of telomerase.

Viruses implicated in human cancer development such as Epstein Barr virus (EBV, related to B cell malignancies and nasopharyngeal carcinomas) and Human Papilloma virus (HPV 16 and 18, related to cervical carcinomas) have long been known to have the capacity to immortalize human cells. It has now been demonstrated that induction of telomerase activity is the key element in this process (Klingelhutz et al., 1996, *Nature* 380, 79-82).

Telomerase is therefore a potential target for cancer therapy. Thus, telomerase inhibitors have been proposed as a new class of anti-cancer drugs (reviewed in Sharma et al., 1997, *Ann Oncol* 8(11), 1063-1074; Axelrod, 1996, *Nature Med* 2(2), 158-159; Huminiecki, 1996, *Acta Biochim Pol* 43(3), 531-538). It has been suggested that the identification of a human telomerase catalytic subunit may provide a biochemical reagent for identifying such drugs (Meyerson et al., 1990, *Cell* 1197, 785-795). Telomerase has also been suggested to be a marker for diagnosis or prognosis of cancer (Soria and Rixe, 1997, *Bull Cancer* 84(10), 963-970; Dahse et al., 1997, *Clin Chem* 43 (5), 708-714).

As far as we are aware, however, no one has previously suggested that telomerase may function as a useful target for T cell mediated therapy, or that telomerase peptides or proteins may be used for the treatment or prophylaxis of cancer.

In accordance with one aspect of the invention, we provide a telomerase protein or peptide for use in a method of treatment or prophylaxis of cancer.

In accordance with a second aspect of the invention, there is provided a nucleic acid for use in a method of treatment or prophylaxis of cancer, the nucleic acid being capable of encoding a telomerase protein or peptide as provided in the first aspect of this invention.

We provide, in accordance with a third aspect of this invention, a pharmaceutical composition comprising at least one telomerase protein or peptide or nucleic acid as provided in the first or second aspect of this invention and a pharmaceutically acceptable carrier or diluent.

According to a fourth aspect of this invention, we provide a method for the preparation of a pharmaceutical composition as provided in the third aspect of the invention, the method comprising mixing at least one telomerase protein or peptide or nucleic acid as provided in the first or second aspect of the invention with a pharmaceutically acceptable carrier or diluent.

There is further provided, according to a fifth aspect of this invention, a pharmaceutical composition comprising a combination of at least one telomerase protein or peptide as provided in the first aspect of this invention and at least one peptide capable of inducing a T cell response against an oncogene or mutant tumor suppressor protein or peptide, together with a pharmaceutically acceptable carrier or diluent.

We further provide, in accordance with a sixth aspect of this invention, a method for the preparation of a pharmaceutical composition as provided in the fifth aspect of this invention, the method comprising mixing at least one telomerase protein or peptide provided in the first aspect of this invention, with at least one peptide capable of inducing a T cell response against an oncogene or tumor suppressor protein or peptide, and a pharmaceutically acceptable carrier or diluent.

In accordance with a seventh aspect of this invention, we provide the use, in the preparation of a medicament for the treatment or prophylaxis of cancer, of a telomerase protein or peptide, or a nucleic acid capable of encoding a telomerase protein or peptide.

According to an eighth aspect of this invention, there is provided a method of generating T lymphocytes capable of recognizing and destroying tumor cells in a mammal, comprising taking a sample of T lymphocytes from a mammal, and culturing the T lymphocyte sample in the presence of telomerase protein or peptide in an amount sufficient to generate telomerase protein or peptide specific T lymphocytes.

The invention is more particularly described, by way of example only, with reference to the accompanying drawing, in which:

FIG. 1 shows the sequences of the conserved amino acid motifs in the human telomerase catalytic subunit, as identified by Meyerson et al. (1997, Cell 90, 785-795) and Nakamura et al. (1997, Science 277, 955-959). Motifs T, 1, 2, 3 (A of Nakamura), 4 (B' of Nakamura), 5 (C of Nakamura), 6 (D of Nakamura) and E are shown. Peptides may be synthesized with sequences corresponding to or encompassing any of the bracketed regions. The designations A2, A1, A3 and B7 indicate peptides that are likely to be presented by HLA-A2, HLA-A1, HLA-A3 and HLA-B7, respectively.

We provide a telomerase protein or peptide for use in a method of treatment or prophylaxis of cancer. In a preferred embodiment, the method comprises generating a T cell response against telomerase. The method may comprise administering to a mammal, preferably a human, suffering or likely to suffer from cancer, a therapeutically effective amount of the telomerase protein or peptide so that a T cell response against the telomerase is induced in the mammal.

Telomerase specific T cells may be used to target cells that express telomerase. Thus, since most cells in the body of an organism do not express telomerase, they will be unaffected. However, tumor cells that express telomerase will be targeted and destroyed. As telomerase activity has been detected in the majority of cancers identified so far, we expect our materials and methods to have widespread utility.

Cancers that are suitable for treatment include, but are not limited to, breast cancer, prostate cancer, pancreatic cancer, colo-rectal cancer, lung cancer, malignant melanoma, leukemias, lymphomas, ovarian cancer, cervical cancer and biliary tract carcinomas.

As used here, the term telomerase denotes a ribonucleoprotein enzyme that has telomere elongating activity. Telomerase protein as used here denotes any protein component of telomerase, including any subunit having catalytic activity.

Preferably the telomerase protein is a mammalian telomerase protein, and most preferably a human telomerase protein. The human telomerase protein is preferably the telomerase catalytic subunit identified as hTRT by Nakamura et al. (1997, Science 277, 955-959) and hEST2 by Meyerson et al. (1990, Cell 1197, 785-795), the cDNA sequences of which are deposited as GenBank accession numbers AF015950 and AF018167, respectively.

The term telomerase peptide as used here means a peptide that has an amino acid sequence corresponding to a sequence present in the amino acid sequence of a telomerase protein. The telomerase peptides preferably contain between 8 and 25 amino acids. More preferably, the telomerase peptides contain between 9 and 25 amino acids. For instance, the telomerase peptides contain 9, 12, 13, 16 or 21 amino acids.

The telomerase protein or peptide is chosen so that it is capable of generating a T cell response directed against the telomerase protein (or against the telomerase protein from which the telomerase peptide is derived). In preferred embodiments, the T cell response induced is a cytotoxic T cell response. The cytotoxic T cell response may be a CD4+ T cell response, or it may be a CD8+ T cell response. In any case, the peptide must be capable of being presented as a complex with an MHC class I or class II protein on the surface of tumor cells or antigen presenting cells, with antigen processing taking place beforehand if necessary.

The telomerase peptide may include one or more amino acid residues from an amino acid motif essential for the biological function of the telomerase protein; in other words, it may overlap at least partially with such an amino acid motif. Examples of such amino acid motifs are motifs 1 to 6 of the human telomerase catalytic subunit sequence hEST2 as identified by Meyerson et al. (1990, Cell 1197, 785-795), in other words, from the motifs LLRSFFYVTE (SEQ ID NO:21),
SRLRFIPK (SEQ ID NO:22),
LRPIVNMDYVVG (SEQ ID NO:23),
PELYFVKVDVTGAYDTI (SEQ ID NO:24),
KSYVQCQGIPQGSILSTLLCSLCY (SEQ ID NO:25),
LLLRLVDDFLLVT (SEQ ID NO:26) and
GCVVNLRKTVV (SEQ ID NO:27)

or from any of motifs T, 1, 2, A, B', C, D or E as identified by Nakamura et al. (1997, Science 277, 955-959) in the hTRT sequence, namely, the motifs WLMSVYVVELLRSFFYVTETTFQKNR-
LFFYRKSVWSKLQSIGIRQHLK (SEQ ID NO:28),
EVRQHREARPALLTSRLRFIPKPDG (SEQ ID NO:29),
LRPIVNMDYVVGARTFRREKRAERLTSRV (SEQ ID NO:30),
PPPELYFVKVDVTGAYDTIPQDRLTEVIASIIKP (SEQ ID NO:31),
KSYVQCQGIPQGSILSTLLCSLCYGDMENKLFAGI (SEQ ID NO:32),
LLRLVDDFLLVTPHLTH (SEQ ID NO:33),
AKTFLRTLVRGVPEYGCVVNLRKTVV (SEQ ID NO:34) and
HGLFPWCGLLL (SEQ ID NO:35).

Suitable peptides that may be used in the methods and compositions described here are set out in TABLE 1 as well as in the Sequence Listing at SEQ ID NOs: 1-20.

Another set of suitable peptides derived from elsewhere in the telomerase sequence, that may be used in the methods and compositions described here, are set out in TABLE 2. The peptides of TABLES 1 and 2 comprise SEQ ID NOs: 1-4, 9-11, 14-15, 17-18, 20, and 36-231 of the Sequence Listing.

Also included are proteins and peptides having amino acid sequences corresponding to an amino acid sequence present in the amino acid sequence of mammalian homologues of the

*Tetrahymena* telomerase associated proteins p80 and p95. For example, the p80 homologues TP1 and TLP1 (Harrington et al., 1997, *Science* 275, 973-977; Nakayama et al., 1997, *Cell* 88, 875-884).

Larger peptide fragments carrying a few amino acid substitutions at either the N-terminal end or the C-terminal end are also included, as it has been established that such peptides may give rise to T cell clones having the appropriate specificity.

The peptides described here are particularly suited for use in a vaccine capable of safely eliciting either CD4+ or CD8+ T cell immunity:

(a) the peptides are synthetically produced and therefore do not include transforming cancer genes or other sites or materials that might produce deleterious effects, (b) the peptides may be used alone to induce cellular immunity, (c) the peptides may be targeted for a particular type of T cell response without the side effects of other unwanted responses.

The telomerase peptides or proteins described here can be administered in an amount in the range of 1 microgram (1 μg) to 1 gram (1 g) to an average human patient or individual to be vaccinated. It is preferable to use a smaller dose in the range of 1 microgram (1 μg) to 1 milligram (1 mg) for each administration.

In preferred embodiments, the telomerase protein or peptide is provided to the patient in the form of a pharmaceutical composition. The telomerase protein or peptide may be administered as a mixture of proteins or a mixture of proteins and peptides or a mixture of peptides. The pharmaceutical composition may in addition include the usual additives, diluents, stabilizers or the like as known in the art.

The pharmaceutical composition may comprise one or more telomerase proteins or peptides. The protein or peptide mixture may be anyone of the following:

(a) a mixture of peptides having different sequences, for example, corresponding to different portions of a telomerase protein sequence;

(b) a mixture of peptides having overlapping sequences, but suitable to fit different HLA alleles;

(c) a mixture of both mixtures (a) and (b);

(d) a mixture of several mixtures (a);

(e) a mixture of several mixtures (b);

(f) a mixture of several mixtures (a) and several mixtures (b);

In each case, a mixture of proteins or peptides corresponding to different telomerase proteins, for example, a telomerase catalytic subunit and a *Tetrahymena* p80 or p95 homologue, may also be used.

Alternatively, the telomerase peptides in the mixture may be covalently linked with each other to form larger polypeptides or even cyclic polypeptides. The pharmaceutical composition may be made by mixing the telomerase protein(s) or peptide(s) with a pharmaceutically acceptable carrier or diluent.

The pharmaceutical composition may also include at least one peptide capable of inducing a T cell response against an oncogene or mutant tumor suppressor protein or peptide. Alternatively, the telomerase proteins or peptides may be administered either simultaneously or in optional sequence with these peptides. Examples of oncogene proteins are the p21-ras proteins H-ras, K-ras and N-ras, abl, gip, gsp, ret and trk. Preferably, the oncogene protein or peptide is a p21-ras protein or peptide, for example, the p21-ras peptides described in our International Application PCT/NO92/00032 (publication number WO92/14756). Tumor suppressor proteins include p53 and Rb (retinoblastoma). Such a pharmaceutical composition may be made by mixing the telomerase protein(s) or peptide(s) with the mutant tumor suppressor or oncogene proteins or peptides, together with a pharmaceutically acceptable carrier or diluent.

As used here, the term mutant refers to a wild type sequence that has one or more of the following: point mutation (transition or transversion), deletion, insertion, duplication, translocation or inversion. The term pharmaceutical composition not only encompasses a composition usable in treatment of cancer patients but also includes compositions useful in connection with prophylaxis, i.e., vaccine compositions.

The telomerase peptides or proteins are administered to a human individual in need of such treatment or prophylaxis. The administration may take place one or several times as suitable to establish and/or maintain the wanted T cell immunity. The peptides may be administered together, either simultaneously or separately, with compounds such as cytokines and/or growth factors, i.e., interleukin-2 (IL-2), interleukin-12 (IL-12), granulocyte macrophage colony stimulating factor (GM-CSF) or the like in order to strengthen the immune response as known in the art. The telomerase proteins or peptides can be used in a vaccine or a therapeutical composition either alone or in combination with other materials. For example, the peptide or peptides may be supplied in the form of a lipopeptide conjugate which is known to induce a high-affinity cytotoxic T cell response (Deres, 1989, Nature 342).

The peptides and proteins mentioned above as possible constituents of the pharmaceutical composition may be provided in the form of nucleic acid encoding the particular peptide or protein. Thus, the pharmaceutical composition may consist of peptide and/or protein alone, or in combination with nucleic acid, or it may consist of mixtures of nucleic acids.

The telomerase peptides or proteins may be administered to an individual in the form of DNA vaccines. The DNA encoding the telomerase peptide or protein may be in the form of cloned plasmid DNA or synthetic oligonucleotide. The DNA may be delivered together with cytokines, such as IL2/ and/or other co-stimulatory molecules. The cytokines and/or co-stimulatory molecules may themselves be delivered in the form of plasmid or oligonucleotide DNA.

The response to a DNA vaccine has been shown to be increased by the presence of immunostimulatory DNA sequences (ISS). These can take the form of hexameric motifs containing methylated CpG, according to the formula: 5'-purine-purine-CG-pyrimidine-pyrimidine-3'. Our DNA vaccines may therefore incorporate these or other ISS, in the DNA encoding the telomerase peptide or protein, in the DNA encoding the cytokine or other co-stimulatory molecules, or in both. A review of the advantages of DNA vaccination is provided by Tighe et al. (1998, *Immunology Today* 19(2), 89-97).

We describe a method of treatment of a patient afflicted with cancer, the method comprising eliciting T-cell responses through stimulating in vivo or ex vivo with a telomerase protein or peptide. The telomerase protein or peptide can also be used in a method of vaccination of a patient in order to obtain resistance against cancer. A suitable method of vaccination comprises eliciting T-cell responses through stimulating in vivo or ex vivo with a telomerase protein or peptide. We also describe a method of treatment or prophylaxis of cancer, comprising administering to a mammal suffering or likely to suffer from cancer a therapeutically effective amount of a telomerase protein or peptide so that a T cell response against telomerase is induced in the mammal.

The peptides described here may be produced by conventional processes, for example, by the various peptide synthesis methods known in the art. Alternatively, they may be fragments of a telomerase protein produced by cleavage, for example, using cyanogen bromide, and subsequent purification. Enzymatic cleavage may also be used. The telomerase proteins or peptides may also be in the form of recombinant expressed proteins or peptides.

Nucleic acids encoding the telomerase peptide can be made by oligonucleotide synthesis. This may be done by any of the various methods available in the art. A nucleic acid encoding telomerase protein may be cloned from a genomic or cDNA library, using conventional library screening. The probe may correspond to a portion of any sequence of a known telomerase gene. Alternatively, the nucleic acid can be obtained by using the Polymerase Chain Reaction (PCR). The nucleic acid is preferably DNA and may suitably be cloned into a vector. Subclones may be generated by using suitable restriction enzymes. The cloned or subcloned DNA may be propagated in a suitable host, for example a bacterial host. Alternatively, the host can be a eukaryotic organism, such as yeast or baculovirus. The telomerase protein or peptides may be produced by expression in a suitable host. In this case, the DNA is cloned into an expression vector. A variety of commercial expression kits are available. The methods described in Maniatis et al. (1991, *Molecular Cloning: A Laboratory Manual*, Cold Spring Harbor, N.Y., Cold Spring Harbor Laboratory Press) and Harlow and Lane (1988, *Antibodies: A Laboratory Manual*, Cold Spring Harbor, N.Y., Cold Spring Harbor Laboratory Press) may be used for these purposes.

Experimental Methods

The peptides were synthesized by using continuous flow solid phase peptide synthesis. N-a-Fmoc-amino acids with appropriate side chain protection were used. The Fmoc-amino acids were activated for coupling as pentafluorophenyl esters or by using either TBTU or diisopropyl carbodiimide activation prior to coupling. 20% piperidine in DMF was used for selective removal of Fmoc after each coupling. Cleavage from the resin and final removal of side chain protection was performed by 95% TFA containing appropriate scavengers. The peptides were purified and analyzed by reversed phase (C18) HPLC. The identity of the peptides was confirmed by using electro-spray mass spectroscopy (Finnigan mat SSQ710).

In order for a cancer vaccine and methods for specific cancer therapy based on T cell immunity to be effective, three conditions must be met:

(a) the peptide is at least 8 amino acids long and is a fragment of a telomerase protein and (b) the peptide is capable of inducing, either in its full length or after processing by antigen presenting cell, T cell responses.

The following experimental methods may be used to determine if these three conditions are met for a particular peptide. First, it should be determined if the particular peptide gives rise to T cell immune responses in vitro. It will also need to be established if the synthetic peptides correspond to, or are capable after processing to yield, peptide fragments corresponding to peptide fragments occurring in cancer cells harboring telomerase or antigen presenting cells that have processed naturally occurring telomerase. The specificity of T cells induced in vivo by telomerase peptide vaccination may also be determined.

It is necessary to determine if telomerase expressing tumor cell lines can be killed by T cell clones obtained from peripheral blood from carcinoma patients after telomerase peptide vaccination. T cell clones are obtained after cloning of T-cell blasts present in peripheral blood mononuclear cells (PBMC) from a carcinoma patient after telomerase peptide vaccination. The peptide vaccination protocol includes several in vivo injections of peptides intracutaneously with GM-CSF or another commonly used adjuvant. Cloning of T cells is performed by plating responding T cell blasts at 5 blasts per well onto Terasaki plates. Each well contains $2\times10^4$ autologous, irradiated (30 Gy) PBMC as feeder cells. The cells are propagated with the candidate telomerase peptide at 25 mM and 5 U/ml recombinant interleukin-2 (rIL-2) (Amersham, Aylesbury, UK) in a total volume of 20 mL. After 9 days, T cell clones are transferred onto flat-bottomed 96-well plates (Costar, Cambridge, Mass.) with 1 mg/ml phytohemagglutinin (PHA, Wellcome, Dartford, UK), 5 U/ml rIL-2 and allogenic irradiated (30 Gy) PBMC ($2\times10^5$) per well as feeder cells. Growing clones are further expanded in 24-well plates with PHA/mL-2 and $1\times10^6$ allogenic, irradiated PBMC as feeder cells and screened for peptide specificity after 4 to 7 days.

T cell clones are selected for further characterization. The cell-surface phenotype of the T cell clone is determined to ascertain if the T cell clone is CD4+ or CD8+. T cell clone is incubated with autologous tumor cell targets at different effector to target ratios to determine if lysis of tumor cells occurs. Lysis indicates that the T cell has reactivity directed against a tumor derived antigen, for example, telomerase protein.

In order to verify that the antigen recognized is associated with telomerase protein, and to identify the HLA class I or class II molecule presenting the putative telomerase peptide to the T cell clone, different telomerase expressing tumor cell lines carrying one or more HLA class I or II molecules in common with those of the patient are used as target cells in cytotoxicity assays. Target cells are labelled with $^{51}Cr$ or $^3H$-thymidine ($9.25\times10^4$ Bq/mL) overnight, washed once and plated at 5000 cells per well in 96 well plates. T cells are added at different effector to target ratios and the plates are incubated for 4 hours at 37° C. and then harvested before counting in a liquid scintillation counter (Packard Topcount). For example, the bladder carcinoma cell line T24 ($12Val^+$, $HLA-Al^+$, $B35^+$), the melanoma cell line FMEX ($12Val^+$, $HLA-A2^+$, $B35^+$) and the colon carcinoma cell line SW 480 ($12Val^+$, $HLA-A2^+$, $B8^+$) or any other telomerase positive tumor cell line may be used as target cells. A suitable cell line that does not express telomerase protein may be used as a control and should not be lysed. Lysis of a particular cell line indicates that the T cell clone being tested recognizes an endogenously-processed telomerase epitope in the context of the HLA class I or class II subtype expressed by that cell line.

The HLA class I or class II restriction of a T cell clone may be determined by blocking experiments. Monoclonal antibodies against HLA class I antigens, for example the panreactive HLA class I monoclonal antibody W6/32, or against class II antigens, for example, monoclonals directed against HLA class II DR, DQ and DP antigens (B8/11, SPV-L3 and B7/21), may be used. The T cell clone activity against the autologous tumor cell line is evaluated using monoclonal antibodies directed against HLA class I and class II molecules at a final concentration of 10 mg/ml. Assays are set up as described above in triplicate in 96 well plates and the target cells are preincubated for 30 minutes at 37° C. before addition of T cells.

The fine specificity of a T cell clone may be determined using peptide pulsing experiments. To identify the telomerase peptide actually being recognized by a T cell clone, a panel of nonamer peptides is tested. $^{51}Cr$ or $^3H$-thymidine labelled, mild acid eluted autologous fibroblasts are plated at 2500 cells per well in 96 well plates and pulsed with the peptides at a concentration of 1 mM together with b2-microglobulin (2.5 mg/mL) in a 5% $CO_2$ incubator at 37° C. before addition of the T cells. Assays are set up in triplicate in 96 well plates and incubated for 4 hours with an effector to target ratio of 5 to 1. Controls can include T cell clone cultured alone, with APC in the absence of peptides or with an irrelevant melanoma associated peptide MART-1/Melan-A peptide.

An alternative protocol to determine the fine specificity of a T cell clone may also be used. In this alternative protocol, the TAP deficient T2 cell line is used as antigen presenting cells. This cell line expresses only small amounts of HLA-A2 antigen, but increased levels of HLA class I antigens at the cell surface can be induced by addition of b2-microglobulin. 3H-labelled target cells are incubated with the different test peptides and control peptides at a concentration of 1 mM together with b2 microglobulin (2.5 mg/mL) for one hour at 37° C. After peptide pulsing, the target cells are washed extensively, counted and plated at 2500 cells per well in 96 well plates before addition of the T cells. The plates are incubated for 4 hours at 37° C. in 5% $CO_2$ before harvesting. Controls include T cell clone cultured alone or with target cells in the absence of peptides. Assays are set up in triplicate in 96 well plates with an effector to target ratio of 20 to 1.

The sensitivity of a T cell clone to a particular peptide identified above may also be determined using a dose-response experiment. Peptide-sensitized fibroblasts can be used as target cells. The target cells are pulsed with the particular peptide as described above for fine specificity determination, with the exception that the peptides are added at different concentrations before the addition of T cells. Controls include target cells alone and target cells pulsed with the irrelevant melanoma associated peptide Melan-A/Mart-1.

BIOLOGICAL EXPERIMENTS

Figure 1:
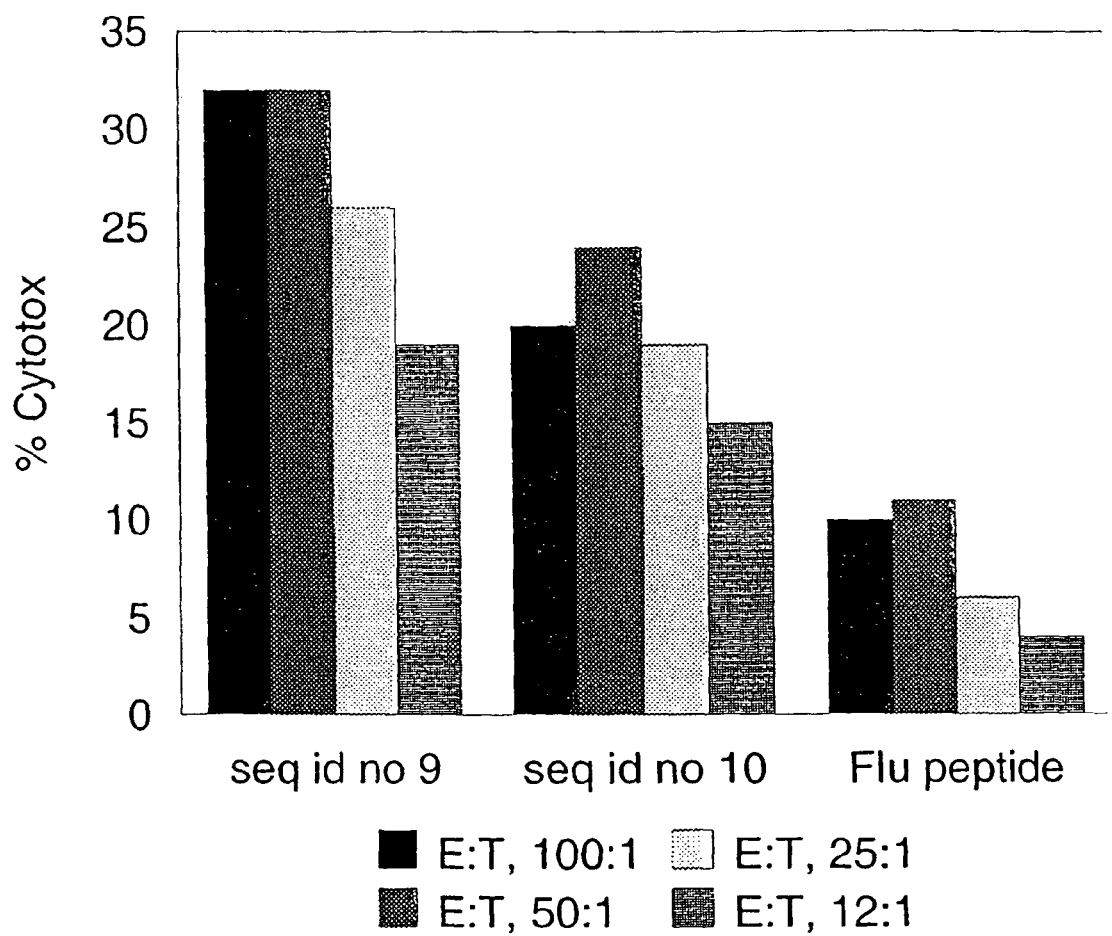
FIG. 1 (FIG. 1) describes the induction of telomerase (hTERT) reactive cytotoxic T lymphocytes (CTLs) in HLA-A2 ($A2/K^b$) transgenic mice immunized with telomerase peptides with SEQ ID NOs: 9 and 10. A standard HLA-A2 restricted influenza (58-66) peptide was used as a control. Three groups of five mice each were given two weekly subcutaneous injections of $10^7$ irradiated, peptide pulsed (100 µg/ml) syngeneic spleen cells. One week after the second injection, the mice were sacrificed and their spleens harvested. Spleen cells were prepared by standard techniques, and cells from primed animals were restimulated in vitro for 5 days by co-culture with peptide pulsed (10 µg/ml) irradiated autologous spleen cells as antigen presenting cells before testing of cytotoxicity against hTERT expressing target cells (Jurkat) transfected with HLA-A2 ($A2/K^b$) in a $^{51}Cr$ release assay.

Columns to the left of FIG. 1 show killing of HLA-A2 transfected Jurkat cells pulsed with the control peptide (influenza 58-66) by T cells obtained after priming of mice with the peptide with SEQ ID NO:9, at different effector to target ratios. Specific cytotoxicity above background was observed at all effector to target ratios. Columns in the middle show similar data with T cells obtained from mice primed with the peptide with SEQ ID NO:10. Significant killing of Jurkat cells was only observed when spleen cells from telomerase peptide pulsed mice were used as effector cells. Thus when spleen cells from influenza peptide primed mice were used as effectors, only background level of killing of Jurkat cells was seen when the target cells were pulsed with an irrelevant peptide (melanocortin receptor 1 peptide, MC1R244) as evident from columns in the right part of FIG. 1. These results demonstrate that the peptides with SEQ ID NOs: 9 and 10 are immunogenic in vivo and upon immunization may elicit an immune response in a warm blooded animal carrying the common human MHC molecule HLA-A2. This finding indicates that the peptides with SEQ ID NOs: 9 and 10 may also be used as a cancer vaccine in humans carrying HLA-A2 and other HLA class I molecules capable of binding these peptides. Furthermore, these results demonstrate that hTERT expressed by the T cell leukemia line Jurkat can be processed by the proteolytic machinery of the cell line to yield peptide fragments identical with or similar to the peptides with SEQ ID NOs: 9 and 10. Together these observations indicate that an immune response obtained after vaccination of cancer patients or patients at risk of developing cancer with these peptides may result in efficient killing of tumor cells expressing the hTERT subunit of telomerase.

FIG. 1 depicts cytotoxicity of HLA-A2 transfected Jurkat cells with effector cells obtained from mice immunized as indicated in the figure. Target cells were labeled with $^{51}Cr$ (0.1 µCi/100 µl cell suspension) for 1 hour at 37° C., washed twice and pulsed with peptide (1 µg/ml) for 1 hour at 37° C. before washing. Two thousand labeled, peptide pulsed target cells were seeded per well in a 96 well v-bottom microtitre plate, and effector cells (from $2.5 \times 10^4$ to $2 \times 10^5$) were added to the wells. Cultures were incubated for 4 hours at 37° C. and supernatants were harvested and tested in a gamma-counter. The results in FIG. 1 are expressed as specific cytotoxicity calculated by the following formula:

(cpm experimental released–cpm spontaneously released)/(cpm total–cpm spontaneously released)×100

Figure 2:
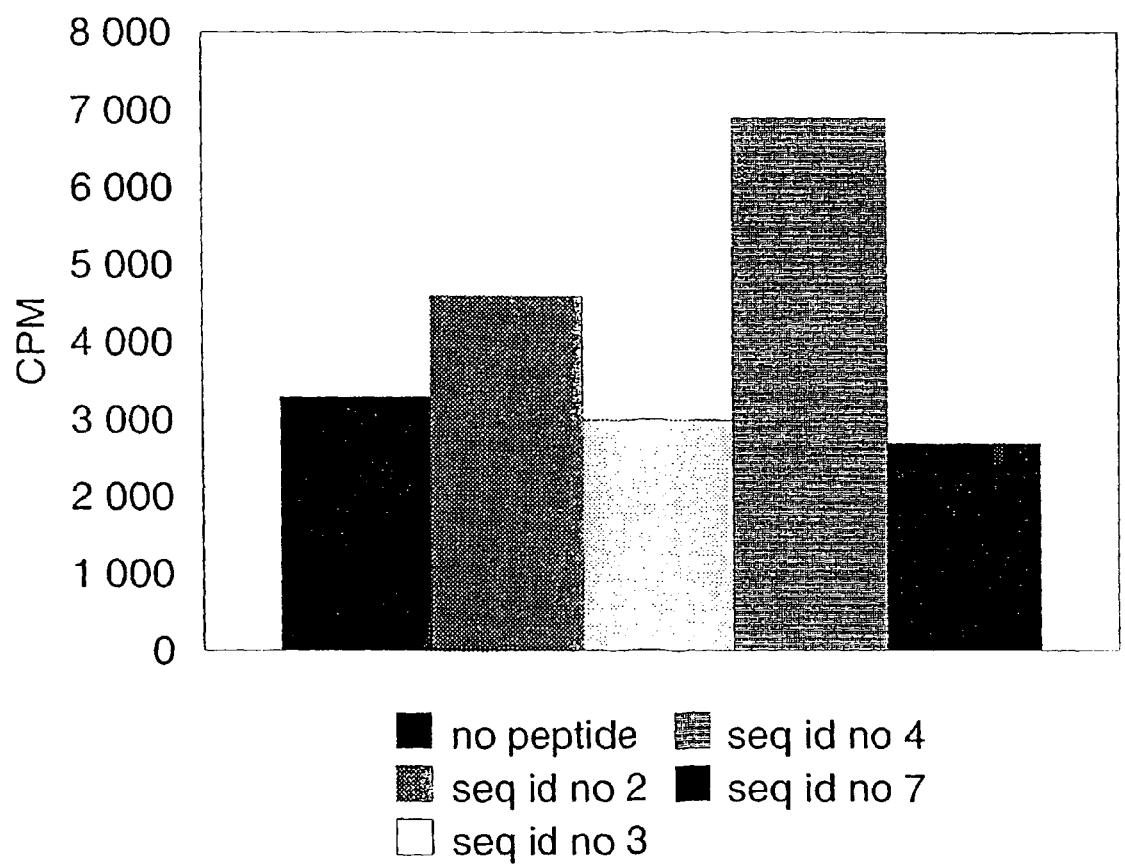

FIG. 2 (FIG. 2) shows the results of in vitro stimulation of peripheral blood T cells from a patient (TT) with colon cancer with telomerase (hTERT) derived peptides SEQ ID NOs: 2, 3, 4 and 7. In vitro culture was performed as follows: Triplicates of 105 mononuclear cells were incubated for 6 days in X-VIVO 10 medium supplemented with 15% pooled heat inactivated human serum in a humidified incubator in 5% $CO_2$. Peptides were present throughout culture at a final concentration of 30 µg/ml in the medium. Cultures without peptide served as control. A proliferative response above background values was seen when the T cells were stimulated with the peptide with SEQ ID NO:4. These results demonstrate that blood from a cancer patient contains circulating T cells specific for a peptide derived from telomerase (hTERT). These results also demonstrate that the enzymatic subunit of telomerase (hTERT) is immunogenic in man and may spontaneously give rise to telomerase specific T cell responses when overexpressed by a tumor growing in the patient. Furthermore, one component of the telomerase specific response in this patient is directed against the peptide with SEQ ID NO:4 described here. This finding indicates that the peptide with SEQ ID NO:4 may also be used as a cancer vaccine in humans. The figure depicts the results of conventional T cell proliferative assays, where peripheral blood mononuclear cells ($10^5$) were cultured with peptides as indicated for 7 days in triplicates before harvesting. To measure the proliferative capacity of the cultures, 3H-thymidine ($3.7 \times 10^4$ Bq/well) was added to the culture overnight before harvesting. Values are given as mean counts per minute (cpm) of the triplicates.

Figure 3:
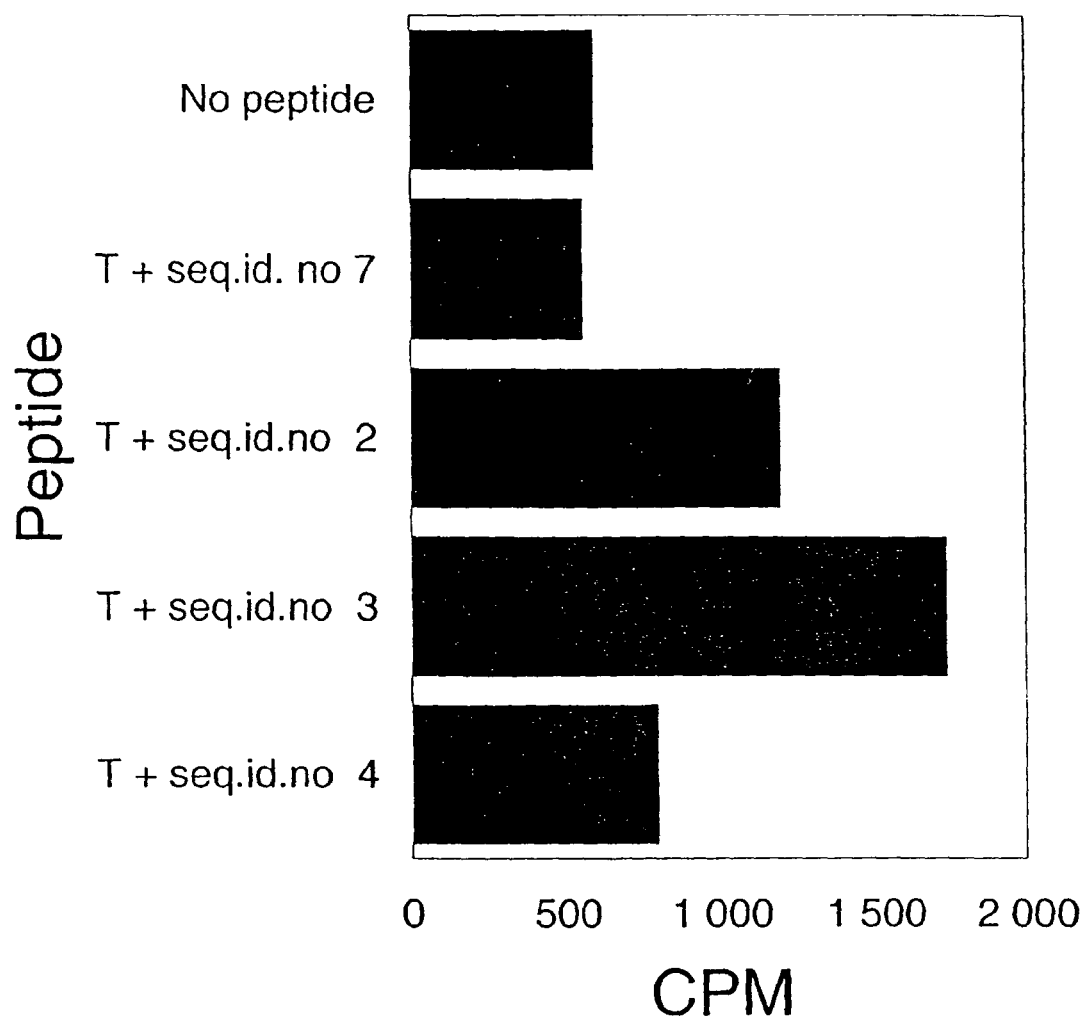
Figure 4:
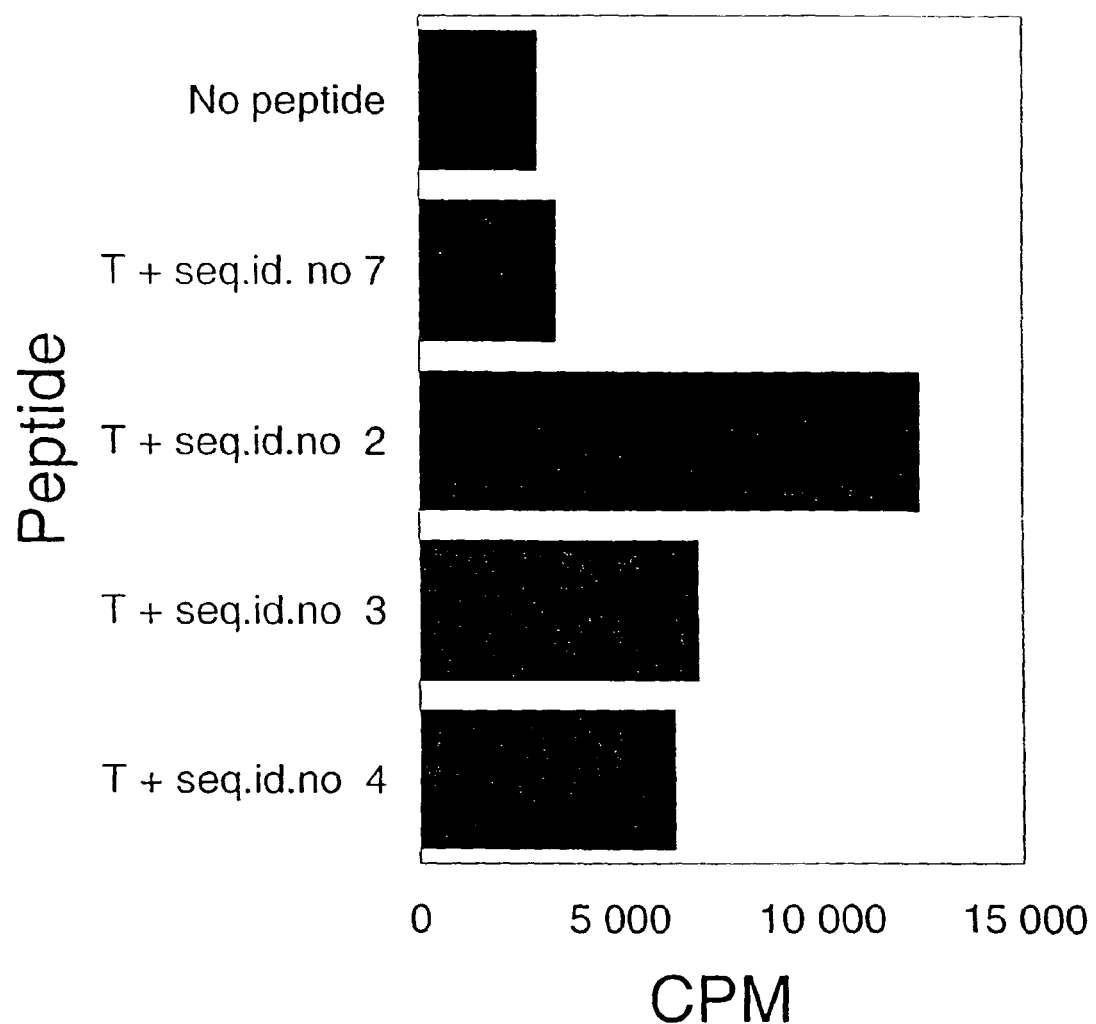

FIGS. 3 and 4 (FIG. 3 and FIG. 4) show the reactivity of tumor infiltrating lymphocytes (TILs) obtained from a patient with advanced pancreatic cancer. The T cells were obtained from a tumor biopsy and were successfully propagated in vitro to establish a T cell line. The T cell line was CD3+, CD4+ and CD8−, and proliferated specifically in response to the telomerase peptides. The results in FIG. 3 show T cells that recognize the peptides with SEQ ID NOs: 2 and 3 when compared to controls with medium alone. The results in FIG. 4 show T cells that recognize the peptide with SEQ ID NO:2. The TILs were expanded by co-culturing with recombinant human interleukin 2 (rIL-2) and tested after 14 days in standard proliferation assay using peptides with SEQ ID NOs: 2, 3, 4 and 7.

TABLE 1

| | |
|---|---|
| LMSVYVVEL | (SEQ ID NO: 11) |
| ELLRSFFYV | (SEQ ID NO: 10) |
| YVVELLRSF | (SEQ ID NO: 36) |
| VVELLRSFF | (SEQ ID NO: 37) |
| SVYVVELLR | (SEQ ID NO: 38) |
| VELLRSFFY | (SEQ ID NO: 39) |
| YVTETTFQK | (SEQ ID NO: 40) |
| RLFFYRKSV | (SEQ ID NO: 41) |
| SIGIRQHLK | (SEQ ID NO: 42) |
| RPALLTSRL | (SEQ ID NO: 17) |
| ALLTSRLRF | (SEQ ID NO: 15) |
| LLTSRLRFI | (SEQ ID NO: 14) |
| RPIVNMDYV | (SEQ ID NO: 43) |
| LRPIVNMDY | (SEQ ID NO: 44) |
| YVVGARTFR | (SEQ ID NO: 45) |
| VVGARTFRR | (SEQ ID NO: 46) |
| GARTFRREK | (SEQ ID NO: 47) |
| ARTFRREKP | (SEQ ID NO: 48) |
| PPELYFVKV | (SEQ ID NO: 49) |
| ELYFVKVDV | (SEQ ID NO: 50) |
| FVKVDVTGA | (SEQ ID NO: 51) |
| IPQDRLTEV | (SEQ ID NO: 52) |
| DRLTEVIAS | (SEQ ID NO: 53) |
| RLTEVIASI | (SEQ ID NO: 54) |
| IPQGSILSTL | (SEQ ID NO: 55) |
| ILSTLLCSL | (SEQ ID NO: 56) |
| LLRLVDDFL | (SEQ ID NO: 57) |
| RLVDDFLLV | (SEQ ID NO: 58) |
| VPEYGCVVN | (SEQ ID NO: 59) |
| VPEYGCVVNL | (SEQ ID NO: 60) |
| TLVRGVPEY | (SEQ ID NO: 61) |
| FLRTLVRGV | (SEQ ID NO: 62) |
| GVPEYGCVV | (SEQ ID NO: 63) |

TABLE 1-continued

| | |
|---|---|
| VVNLRKTVV | (SEQ ID NO: 64) |
| GLFPWCGLL | (SEQ ID NO: 65) |
| FLHWLMSVYVVELLRSFFYVTE | (SEQ ID NO: 1) |
| EARPALLTSRLRFIPK | (SEQ ID NO: 2) |
| DGLRPIVNMDYVVGAR | (SEQ ID NO: 3) |
| GVPEYGCVVNLRKVVNF | (SEQ ID NO: 4) |

TABLE 2

| | |
|---|---|
| YAETKHFLY | (SEQ ID NO: 66) |
| ISDTASLCY | (SEQ ID NO: 67) |
| DTDPRRLVQ | (SEQ ID NO: 68) |
| AQDPPPELY | (SEQ ID NO: 69) |
| LTDLQPYMR | (SEQ ID NO: 70) |
| QSDYSSYAR | (SEQ ID NO: 71) |
| ILAKFLHWL | (SEQ ID NO: 9) |
| ELLRSFFYV | (SEQ ID NO: 10) |
| LLARCALFV | (SEQ ID NO: 72) |
| WLCHQAFLL | (SEQ ID NO: 73) |
| RLVDDFLLV | (SEQ ID NO: 58) |
| RLFFYRKSV | (SEQ ID NO: 41) |
| LQLPFHQQV | (SEQ ID NO: 74) |
| RLGPQGWRL | (SEQ ID NO: 75) |
| SLQELTWKM | (SEQ ID NO: 76) |
| NVLAFGFAL | (SEQ ID NO: 77) |
| VLLKTHCPL | (SEQ ID NO: 78) |
| FLLVTPHLT | (SEQ ID NO: 79) |
| TLTDLQPYM | (SEQ ID NO: 80) |
| RLTEVIASI | (SEQ ID NO: 54) |
| FLDLQVNSL | (SEQ ID NO: 81) |
| SLNEASSGL | (SEQ ID NO: 82) |
| ILSTLLCSL | (SEQ ID NO: 56) |
| LLGASVLGL | (SEQ ID NO: 83) |
| VLAFGFALL | (SEQ ID NO: 84) |
| LQPYMRQFV | (SEQ ID NO: 85) |
| LMSVYVVEL | (SEQ ID NO: 11) |
| RLPQRYWQM | (SEQ ID NO: 86) |
| RQHSSPWQV | (SEQ ID NO: 87) |
| YLPNTVTDA | (SEQ ID NO: 88) |
| NMRRKLFGV | (SEQ ID NO: 89) |

TABLE 2-continued

| | |
|---|---|
| RLTSRVKAL | (SEQ ID NO: 90) |
| LLQAYRFHA | (SEQ ID NO: 91) |
| LLDTRTLEV | (SEQ ID NO: 92) |
| YMRQFVAHL | (SEQ ID NO: 93) |
| LLTSRLRFI | (SEQ ID NO: 14) |
| CLVCVPWDA | (SEQ ID NO: 94) |
| LLSSLRPSL | (SEQ ID NO: 95) |
| FMCHHAVRI | (SEQ ID NO: 96) |
| LQVNSLQTV | (SEQ ID NO: 97) |
| LVAQCLVCV | (SEQ ID NO: 98) |
| CLKELVARV | (SEQ ID NO: 99) |
| FLRNTKKFI | (SEQ ID NO: 100) |
| ALPSDFKTI | (SEQ ID NO: 101) |
| VLVHLLARC | (SEQ ID NO: 102) |
| VQSDYSSYA | (SEQ ID NO: 103) |
| SVWSKLQSI | (SEQ ID NO: 104) |
| KLPGTTLTA | (SEQ ID NO: 105) |
| QLSRKLPGT | (SEQ ID NO: 106) |
| ELYFVKVDV | (SEQ ID NO: 50) |
| GLLLDTRTL | (SEQ ID NO: 107) |
| WMPGTPRRL | (SEQ ID NO: 108) |
| SLTGARRLV | (SEQ ID NO: 109) |
| VVIEQSSSL | (SEQ ID NO: 110) |
| LPSEAVQWL | (SEQ ID NO: 111) |
| QAYRFHACV | (SEQ ID NO: 112) |
| GLFDVFLRF | (SEQ ID NO: 113) |
| KLFGVLRLK | (SEQ ID NO: 114) |
| RLREEILAK | (SEQ ID NO: 115) |
| TLVRGVPEY | (SEQ ID NO: 61) |
| GLPAPGARR | (SEQ ID NO: 116) |
| GLFPWCGLL | (SEQ ID NO: 65) |
| KLTRHRVTY | (SEQ ID NO: 117) |
| VLPLATFVR | (SEQ ID NO: 118) |
| ELVARVLQR | (SEQ ID NO: 119) |
| DPRRLVQLL | (SEQ ID NO: 120) |
| FVRACLRRL | (SEQ ID NO: 121) |
| SVREAGVPL | (SEQ ID NO: 122) |
| AGRNMRRKL | (SEQ ID NO: 123) |
| LARCALFVL | (SEQ ID NO: 124) |
| RPAEEATSL | (SEQ ID NO: 125) |

TABLE 2-continued

| | |
|---|---|
| LPSDFKTIL | (SEQ ID NO: 126) |
| LPSEAVQWL | (SEQ ID NO: 111) |
| LPGTTLTAL | (SEQ ID NO: 127) |
| RPSFLLSSL | (SEQ ID NO: 128) |
| LPNTVTDAL | (SEQ ID NO: 129) |
| RPALLTSRL | (SEQ ID NO: 17) |
| RCRAVRSLL | (SEQ ID NO: 130) |
| MPRAPRCRA | (SEQ ID NO: 131) |
| GIRRDGLLL | (SEQ ID NO: 132) |
| VLRLKCHSL | (SEQ ID NO: 133) |
| YMRQFVAHL | (SEQ ID NO: 93) |
| SLRTAQTQL | (SEQ ID NO: 134) |
| QMRPLFLEL | (SEQ ID NO: 135) |
| LLRLVDDFL | (SEQ ID NO: 57) |
| FVQMPAHGL | (SEQ ID NO: 136) |
| HASGPRRRL | (SEQ ID NO: 137) |
| VVIEQSSSL | (SEQ ID NO: 110) |
| RVISDTASL | (SEQ ID NO: 138) |
| CVPAAEHRL | (SEQ ID NO: 139) |
| RVKALFSVL | (SEQ ID NO: 140) |
| NVLAFGFAL | (SEQ ID NO: 77) |
| LVARVLQRL | (SEQ ID NO: 141) |
| FAGIRRDGL | (SEQ ID NO: 142) |
| HAQCPYGVL | (SEQ ID NO: 143) |
| RAQDPPPEL | (SEQ ID NO: 144) |
| AYRFHACVL | (SEQ ID NO: 145) |
| HAKLSLQEL | (SEQ ID NO: 146) |
| GAKGAAGPL | (SEQ ID NO: 147) |
| TASLCYSIL | (SEQ ID NO: 148) |
| APRCRAVRS | (SEQ ID NO: 149) |
| GARRLVETI | (SEQ ID NO: 150) |
| AQCPYGVLL | (SEQ ID NO: 151) |
| HAKTFLRTL | (SEQ ID NO: 152) |
| EATSLEGAL | (SEQ ID NO: 153) |
| KAKNAGMSL | (SEQ ID NO: 154) |
| AQTQLSRKL | (SEQ ID NO: 155) |
| AGIRRDGLL | (SEQ ID NO: 156) |
| VLRLKCHSL | (SEQ ID NO: 133) |
| ILKAKNAGM | (SEQ ID NO: 157) |

TABLE 2-continued

| | |
|---|---|
| DPRRLVQLL | (SEQ ID NO: 158) |
| GAKGAAGPL | (SEQ ID NO: 147) |
| FAGIRRDGL | (SEQ ID NO: 142) |
| GARRRGGSA | (SEQ ID NO: 159) |
| HAKTFLRTL | (SEQ ID NO: 152) |
| HAKLSLQEL | (SEQ ID NO: 146) |
| LARCALFVL | (SEQ ID NO: 124) |
| EHRLREEIL | (SEQ ID NO: 160) |
| NMRRKLFGV | (SEQ ID NO: 89) |
| CAREKPQGS | (SEQ ID NO: 161) |
| LTRHRVTYV | (SEQ ID NO: 162) |
| RRFLRNTKK | (SEQ ID NO: 163) |
| RRDGLLLRL | (SEQ ID NO: 164) |
| RREKRAERL | (SEQ ID NO: 165) |
| RRLVETIFL | (SEQ ID NO: 166) |
| LRFMCHHAV | (SEQ ID NO: 167) |
| RRYAVVQKA | (SEQ ID NO: 168) |
| KRAERLTSR | (SEQ ID NO: 169) |
| RRKLFGVLR | (SEQ ID NO: 170) |
| RRRGGSASR | (SEQ ID NO: 171) |
| RRLPRLPQR | (SEQ ID NO: 172) |
| RRLGPQGWR | (SEQ ID NO: 173) |
| LRGSGAWGL | (SEQ ID NO: 174) |
| HREARPALL | (SEQ ID NO: 175) |
| VRRYAVVQK | (SEQ ID NO: 176) |
| ARTSIRASL | (SEQ ID NO: 177) |
| HRVTYVPLL | (SEQ ID NO: 178) |
| LRSHYREVL | (SEQ ID NO: 179) |
| MRPLFLELL | (SEQ ID NO: 180) |
| HRAWRTFVL | (SEQ ID NO: 181) |
| MRRKLFGVL | (SEQ ID NO: 182) |
| LRLVDDFLL | (SEQ ID NO: 183) |
| LRRVGDDVL | (SEQ ID NO: 184) |
| YRKSVWSKL | (SEQ ID NO: 185) |
| QRLCERGAK | (SEQ ID NO: 186) |
| FRALVAQCL | (SEQ ID NO: 187) |
| SRKLPGTTL | (SEQ ID NO: 188) |
| LRRLVPPGL | (SEQ ID NO: 189) |
| RRSPGVGCV | (SEQ ID NO: 190) |
| RRVGDDVLV | (SEQ ID NO: 191) |

TABLE 2-continued

| | |
|---|---|
| VRGCAWLRR | (SEQ ID NO: 192) |
| VRSLLRSHY | (SEQ ID NO: 193) |
| ARTFRREKR | (SEQ ID NO: 194) |
| SRSLPLPKR | (SEQ ID NO: 195) |
| IRASLTFNR | (SEQ ID NO: 196) |
| LREEILAKF | (SEQ ID NO: 197) |
| IRRDGLLLR | (SEQ ID NO: 198) |
| QRGDPAAFR | (SEQ ID NO: 199) |
| LRPIVNMDY | (SEQ ID NO: 44) |
| ARRLVETIF | (SEQ ID NO: 200) |
| ARPALLTSR | (SEQ ID NO: 18) |
| LRPSLTGAR | (SEQ ID NO: 201) |
| LRLKCHSLF | (SEQ ID NO: 202) |
| FRREKRAER | (SEQ ID NO: 203) |
| ARGGPPEAF | (SEQ ID NO: 204) |
| CRAVRSLLR | (SEQ ID NO: 205) |
| GRTRGPSDR | (SEQ ID NO: 206) |
| RRRLGCERA | (SEQ ID NO: 207) |
| LRELSEAEV | (SEQ ID NO: 208) |
| ARCALFVLV | (SEQ ID NO: 209) |
| RPAEEATSL | (SEQ ID NO: 125) |
| DPRRLVQLL | (SEQ ID NO: 120) |
| RPSFLLSSL | (SEQ ID NO: 128) |
| LPSEAVQWL | (SEQ ID NO: 111) |
| RPALLTSRL | (SEQ ID NO: 17) |
| LPSDFKTIL | (SEQ ID NO: 126) |
| RPPPAAPSF | (SEQ ID NO: 210) |
| LPRLPQRYW | (SEQ ID NO: 211) |
| LPNTVTDAL | (SEQ ID NO: 129) |
| LPGTTLTAL | (SEQ ID NO: 127) |
| LAKFLHWLM | (SEQ ID NO: 212) |
| KAKNAGMSL | (SEQ ID NO: 154) |
| GSRHNERRF | (SEQ ID NO: 213) |
| KALFSVLNY | (SEQ ID NO: 214) |
| SPLRDAVVI | (SEQ ID NO: 215) |
| RAQDPPPEL | (SEQ ID NO: 144) |
| MPAHGLFPW | (SEQ ID NO: 216) |
| AEVRQHREA | (SEQ ID NO: 217) |
| REAGVPLGL | (SEQ ID NO: 218) |

TABLE 2-continued

| | |
|---|---|
| EEATSLEGA | (SEQ ID NO: 219) |
| LEAAANPAL | (SEQ ID NO: 220) |
| QETSPLRDA | (SEQ ID NO: 221) |
| REVLPLATF | (SEQ ID NO: 222) |
| KEQLRPSFL | (SEQ ID NO: 223) |
| REKPQGSVA | (SEQ ID NO: 224) |
| LEVQSDYSS | (SEQ ID NO: 225) |

TABLE 2-continued

| | |
|---|---|
| REARPALLT | (SEQ ID NO: 226) |
| EEDTDPRRL | (SEQ ID NO: 227) |
| REEILAKFL | (SEQ ID NO: 20) |
| CERGAKNVL | (SEQ ID NO: 228) |
| DDVLVHLLA | (SEQ ID NO: 229) |
| GDMENKLFA | (SEQ ID NO: 230) |
| YERARRPGL | (SEQ ID NO: 231) |

What is claimed is:

1. A method of eliciting T cell immunity in a mammalian subject comprising
   (a) stimulating the subject's immune system in vivo or ex vivo with a peptide capable of generating a T cell response directed against telomerase, wherein said peptide is a fragment of telomerase protein consisting of 16 to 25 amino acids and comprising the amino acid sequence set forth in SEQ ID NO: 2, and
   (b) eliciting a T cell response in the subject.

2. The method of claim 1, wherein the peptide consists of the amino acid sequence SEQ ID NO: 2.

3. The method of claim 1, wherein the telomerase includes telomerase expressed by a cancer.

4. The method of claim 3, wherein the cancer is breast cancer, prostate cancer, pancreatic cancer, colo-rectal cancer, lung cancer, malignant melanoma, leukemias, lymphomas, ovarian cancer, cervical cancer, or biliary tract carcinomas.

5. A method of eliciting T cell immunity in a mammalian subject afflicted with a cancer, comprising the step of administering to the subject an effective amount of a composition comprising:
   (a) an isolated peptide capable of generating a T cell response directed against telomerase, wherein said peptide is a fragment of telomerase protein consisting of 16 to 25 amino acids and comprising the amino acid sequence set forth in SEQ ID NO: 2, and
   (b) a carrier or diluent for the peptide.

6. The method of claim 5, wherein the peptide consists of the amino acid sequence SEQ ID NO: 2.

7. The method of claim 6, wherein the composition also contains at least one peptide not containing SEQ ID NO: 2, but which is capable of inducing a T cell response directed against either (i) an oncogene protein or peptide, or (ii) a mutant tumor suppressor protein or peptide.

8. The method of claim 5, wherein the cancer is breast cancer, prostate cancer, pancreatic cancer, colo-rectal cancer, lung cancer, malignant melanoma, leukemias, lymphomas, ovarian cancer, cervical cancer, or biliary tract carcinomas.

* * * * *

UNITED STATES PATENT AND TRADEMARK OFFICE
CERTIFICATE OF CORRECTION

| | | |
|---|---|---|
| PATENT NO. | : 7,794,723 B2 | Page 1 of 1 |
| APPLICATION NO. | : 11/332378 | |
| DATED | : September 14, 2010 | |
| INVENTOR(S) | : Gustav Gaudernack et al. | |

It is certified that error appears in the above-identified patent and that said Letters Patent is hereby corrected as shown below:

ON THE TITLE PAGE COL. 2 — (56) REFERENCES CITED

OTHER PUBLICATIONS
(Page 2) Under Grottier, C.W., et al, "Grottier, C.W., et al." should read
--Greider, C.W., et al.--.

Signed and Sealed this
Ninth Day of April, 2013

Teresa Stanek Rea
*Acting Director of the United States Patent and Trademark Office*

SEQUENCE LISTING

```
<160> NUMBER OF SEQ ID NOS: 231

<210> SEQ ID NO 1
<211> LENGTH: 22
<212> TYPE: PRT
<213> ORGANISM: Homo sapiens, other or unknown

<400> SEQUENCE: 1

Phe Leu His Trp Leu Met Ser Val Tyr Val Val Glu Leu Leu Arg Ser
1               5                   10                  15

Phe Phe Tyr Val Thr Glu
            20

<210> SEQ ID NO 2
<211> LENGTH: 16
<212> TYPE: PRT
<213> ORGANISM: Homo sapiens, other or unknown

<400> SEQUENCE: 2

Glu Ala Arg Pro Ala Leu Leu Thr Ser Arg Leu Arg Phe Ile Pro Lys
1               5                   10                  15

<210> SEQ ID NO 3
<211> LENGTH: 16
<212> TYPE: PRT
<213> ORGANISM: Homo sapiens, other or unknown

<400> SEQUENCE: 3

Asp Gly Leu Arg Pro Ile Val Asn Met Asp Tyr Val Val Gly Ala Arg
1               5                   10                  15

<210> SEQ ID NO 4
<211> LENGTH: 18
<212> TYPE: PRT
<213> ORGANISM: Homo sapiens, other or unknown

<400> SEQUENCE: 4

Gly Val Pro Glu Tyr Gly Cys Val Val Asn Leu Arg Lys Thr Val Val
1               5                   10                  15

Asn Phe

<210> SEQ ID NO 5
<211> LENGTH: 23
<212> TYPE: PRT
<213> ORGANISM: Homo sapiens, other or unknown
```

-continued

```
<400> SEQUENCE: 5

Lys Phe Leu His Trp Leu Met Ser Val Tyr Val Val Glu Leu Leu Arg
1               5                   10                  15

Ser Phe Phe Tyr Val Thr Glu
            20

<210> SEQ ID NO 6
<211> LENGTH: 17
<212> TYPE: PRT
<213> ORGANISM: Homo sapiens, other or unknown

<400> SEQUENCE: 6

Lys Phe Leu His Trp Leu Met Ser Val Tyr Val Val Glu Leu Leu Arg
1               5                   10                  15

Ser

<210> SEQ ID NO 7
<211> LENGTH: 18
<212> TYPE: PRT
<213> ORGANISM: Homo sapiens, other or unknown

<400> SEQUENCE: 7

Leu Met Ser Val Tyr Val Val Glu Leu Leu Arg Ser Phe Phe Tyr Val
1               5                   10                  15

Thr Glu

<210> SEQ ID NO 8

<400> SEQUENCE: 8

000

<210> SEQ ID NO 9
<211> LENGTH: 9
<212> TYPE: PRT
<213> ORGANISM: Homo sapiens, other or unknown

<400> SEQUENCE: 9

Ile Leu Ala Lys Phe Leu His Trp Leu
1               5

<210> SEQ ID NO 10
<211> LENGTH: 9
<212> TYPE: PRT
<213> ORGANISM: Homo sapiens, other or unknown

<400> SEQUENCE: 10

Glu Leu Leu Arg Ser Phe Phe Tyr Val
1               5

<210> SEQ ID NO 11
<211> LENGTH: 9
<212> TYPE: PRT
<213> ORGANISM: Homo sapiens, other or unknown

<400> SEQUENCE: 11

Leu Met Ser Val Tyr Val Val Glu Leu
1               5

<210> SEQ ID NO 12
<211> LENGTH: 9
<212> TYPE: PRT
<213> ORGANISM: Homo sapiens, other or unknown
```

<400> SEQUENCE: 12

Thr Ser Arg Leu Arg Phe Ile Pro Lys
1               5

<210> SEQ ID NO 13
<211> LENGTH: 9
<212> TYPE: PRT
<213> ORGANISM: Homo sapiens, other or unknown

<400> SEQUENCE: 13

Leu Thr Ser Arg Leu Arg Phe Ile Pro
1               5

<210> SEQ ID NO 14
<211> LENGTH: 9
<212> TYPE: PRT
<213> ORGANISM: Homo sapiens, other or unknown

<400> SEQUENCE: 14

Leu Leu Thr Ser Arg Leu Arg Phe Ile
1               5

<210> SEQ ID NO 15
<211> LENGTH: 9
<212> TYPE: PRT
<213> ORGANISM: Homo sapiens, other or unknown

<400> SEQUENCE: 15

Ala Leu Leu Thr Ser Arg Leu Arg Phe
1               5

<210> SEQ ID NO 16
<211> LENGTH: 9
<212> TYPE: PRT
<213> ORGANISM: Homo sapiens, other or unknown

<400> SEQUENCE: 16

Pro Ala Leu Leu Thr Ser Arg Leu Arg
1               5

<210> SEQ ID NO 17
<211> LENGTH: 9
<212> TYPE: PRT
<213> ORGANISM: Homo sapiens, other or unknown

<400> SEQUENCE: 17

Arg Pro Ala Leu Leu Thr Ser Arg Leu
1               5

<210> SEQ ID NO 18
<211> LENGTH: 9
<212> TYPE: PRT
<213> ORGANISM: Homo sapiens, other or unknown

<400> SEQUENCE: 18

Ala Arg Pro Ala Leu Leu Thr Ser Arg
1               5

<210> SEQ ID NO 19
<211> LENGTH: 9
<212> TYPE: PRT
<213> ORGANISM: Homo sapiens, other or unknown

<400> SEQUENCE: 19

```
Glu Ala Arg Pro Ala Leu Leu Thr Ser
1               5

<210> SEQ ID NO 20
<211> LENGTH: 9
<212> TYPE: PRT
<213> ORGANISM: Homo sapiens, other or unknown

<400> SEQUENCE: 20

Arg Glu Glu Ile Leu Ala Lys Phe Leu
1               5

<210> SEQ ID NO 21
<211> LENGTH: 10
<212> TYPE: PRT
<213> ORGANISM: Homo sapiens, other or unknown

<400> SEQUENCE: 21

Leu Leu Arg Ser Phe Phe Tyr Val Thr Glu
1               5                   10

<210> SEQ ID NO 22
<211> LENGTH: 8
<212> TYPE: PRT
<213> ORGANISM: Homo sapiens, other or unknown

<400> SEQUENCE: 22

Ser Arg Leu Arg Phe Ile Pro Lys
1               5

<210> SEQ ID NO 23
<211> LENGTH: 12
<212> TYPE: PRT
<213> ORGANISM: Homo sapiens, other or unknown

<400> SEQUENCE: 23

Leu Arg Pro Ile Val Asn Met Asp Tyr Val Val Gly
1               5                   10

<210> SEQ ID NO 24
<211> LENGTH: 17
<212> TYPE: PRT
<213> ORGANISM: Homo sapiens, other or unknown

<400> SEQUENCE: 24

Pro Glu Leu Tyr Phe Val Lys Val Asp Val Thr Gly Ala Tyr Asp Thr
1               5                   10                  15

Ile

<210> SEQ ID NO 25
<211> LENGTH: 24
<212> TYPE: PRT
<213> ORGANISM: Homo sapiens, other or unknown

<400> SEQUENCE: 25

Lys Ser Tyr Val Gln Cys Gln Gly Ile Pro Gln Gly Ser Ile Leu Ser
1               5                   10                  15

Thr Leu Leu Cys Ser Leu Cys Tyr
                20

<210> SEQ ID NO 26
<211> LENGTH: 13
<212> TYPE: PRT
```

<213> ORGANISM: Homo sapiens, other or unknown

<400> SEQUENCE: 26

Leu Leu Leu Arg Leu Val Asp Asp Phe Leu Leu Val Thr
1               5                   10

<210> SEQ ID NO 27
<211> LENGTH: 11
<212> TYPE: PRT
<213> ORGANISM: Homo sapiens, other or unknown

<400> SEQUENCE: 27

Gly Cys Val Val Asn Leu Arg Lys Thr Val Val
1               5                   10

<210> SEQ ID NO 28
<211> LENGTH: 48
<212> TYPE: PRT
<213> ORGANISM: Homo sapiens, other or unknown

<400> SEQUENCE: 28

Trp Leu Met Ser Val Tyr Val Val Glu Leu Leu Arg Ser Phe Phe Tyr
1               5                   10                  15

Val Thr Glu Thr Thr Phe Gln Lys Asn Arg Leu Phe Phe Tyr Arg Lys
                20                  25                  30

Ser Val Trp Ser Lys Leu Gln Ser Ile Gly Ile Arg Gln His Leu Lys
            35                  40                  45

<210> SEQ ID NO 29
<211> LENGTH: 25
<212> TYPE: PRT
<213> ORGANISM: Homo sapiens, other or unknown

<400> SEQUENCE: 29

Glu Val Arg Gln His Arg Glu Ala Arg Pro Ala Leu Leu Thr Ser Arg
1               5                   10                  15

Leu Arg Phe Ile Pro Lys Pro Asp Gly
            20                  25

<210> SEQ ID NO 30
<211> LENGTH: 29
<212> TYPE: PRT
<213> ORGANISM: Homo sapiens, other or unknown

<400> SEQUENCE: 30

Leu Arg Pro Ile Val Asn Met Asp Tyr Val Val Gly Ala Arg Thr Phe
1               5                   10                  15

Arg Arg Glu Lys Arg Ala Glu Arg Leu Thr Ser Arg Val
                20                  25

<210> SEQ ID NO 31
<211> LENGTH: 34
<212> TYPE: PRT
<213> ORGANISM: Homo sapiens, other or unknown

<400> SEQUENCE: 31

Pro Pro Pro Glu Leu Tyr Phe Val Lys Val Asp Val Thr Gly Ala Tyr
1               5                   10                  15

Asp Thr Ile Pro Gln Asp Arg Leu Thr Glu Val Ile Ala Ser Ile Ile
            20                  25                  30

Lys Pro

```
<210> SEQ ID NO 32
<211> LENGTH: 35
<212> TYPE: PRT
<213> ORGANISM: Homo sapiens, other or unknown

<400> SEQUENCE: 32

Lys Ser Tyr Val Gln Cys Gln Gly Ile Pro Gln Gly Ser Ile Leu Ser
1               5                   10                  15

Thr Leu Leu Cys Ser Leu Cys Tyr Gly Asp Met Glu Asn Lys Leu Phe
            20                  25                  30

Ala Gly Ile
        35

<210> SEQ ID NO 33
<211> LENGTH: 17
<212> TYPE: PRT
<213> ORGANISM: Homo sapiens, other or unknown

<400> SEQUENCE: 33

Leu Leu Arg Leu Val Asp Asp Phe Leu Leu Val Thr Pro His Leu Thr
1               5                   10                  15

His

<210> SEQ ID NO 34
<211> LENGTH: 26
<212> TYPE: PRT
<213> ORGANISM: Homo sapiens, other or unknown

<400> SEQUENCE: 34

Ala Lys Thr Phe Leu Arg Thr Leu Val Arg Gly Val Pro Glu Tyr Gly
1               5                   10                  15

Cys Val Val Asn Leu Arg Lys Thr Val Val
            20                  25

<210> SEQ ID NO 35
<211> LENGTH: 11
<212> TYPE: PRT
<213> ORGANISM: Homo sapiens, other or unknown

<400> SEQUENCE: 35

His Gly Leu Phe Pro Trp Cys Gly Leu Leu Leu
1               5                   10

<210> SEQ ID NO 36
<211> LENGTH: 9
<212> TYPE: PRT
<213> ORGANISM: Homo sapiens, other or unknown

<400> SEQUENCE: 36

Tyr Val Val Glu Leu Leu Arg Ser Phe
1               5

<210> SEQ ID NO 37
<211> LENGTH: 9
<212> TYPE: PRT
<213> ORGANISM: Homo sapiens, other or unknown

<400> SEQUENCE: 37

Val Val Glu Leu Leu Arg Ser Phe Phe
1               5

<210> SEQ ID NO 38
```

```
<211> LENGTH: 9
<212> TYPE: PRT
<213> ORGANISM: Homo sapiens, other or unknown

<400> SEQUENCE: 38

Ser Val Tyr Val Val Glu Leu Leu Arg
1               5

<210> SEQ ID NO 39
<211> LENGTH: 9
<212> TYPE: PRT
<213> ORGANISM: Homo sapiens, other or unknown

<400> SEQUENCE: 39

Val Glu Leu Leu Arg Ser Phe Phe Tyr
1               5

<210> SEQ ID NO 40
<211> LENGTH: 9
<212> TYPE: PRT
<213> ORGANISM: Homo sapiens, other or unknown

<400> SEQUENCE: 40

Tyr Val Thr Glu Thr Thr Phe Gln Lys
1               5

<210> SEQ ID NO 41
<211> LENGTH: 9
<212> TYPE: PRT
<213> ORGANISM: Homo sapiens, other or unknown

<400> SEQUENCE: 41

Arg Leu Phe Phe Tyr Arg Lys Ser Val
1               5

<210> SEQ ID NO 42
<211> LENGTH: 9
<212> TYPE: PRT
<213> ORGANISM: Homo sapiens, other or unknown

<400> SEQUENCE: 42

Ser Ile Gly Ile Arg Gln His Leu Lys
1               5

<210> SEQ ID NO 43
<211> LENGTH: 9
<212> TYPE: PRT
<213> ORGANISM: Homo sapiens, other or unknown

<400> SEQUENCE: 43

Arg Pro Ile Val Asn Met Asp Tyr Val
1               5

<210> SEQ ID NO 44
<211> LENGTH: 9
<212> TYPE: PRT
<213> ORGANISM: Homo sapiens, other or unknown

<400> SEQUENCE: 44

Leu Arg Pro Ile Val Asn Met Asp Tyr
1               5

<210> SEQ ID NO 45
<211> LENGTH: 9
<212> TYPE: PRT
```

<213> ORGANISM: Homo sapiens, other or unknown

<400> SEQUENCE: 45

Tyr Val Val Gly Ala Arg Thr Phe Arg
1               5

<210> SEQ ID NO 46
<211> LENGTH: 9
<212> TYPE: PRT
<213> ORGANISM: Homo sapiens, other or unknown

<400> SEQUENCE: 46

Val Val Gly Ala Arg Thr Phe Arg Arg
1               5

<210> SEQ ID NO 47
<211> LENGTH: 9
<212> TYPE: PRT
<213> ORGANISM: Homo sapiens, other or unknown

<400> SEQUENCE: 47

Gly Ala Arg Thr Phe Arg Arg Glu Lys
1               5

<210> SEQ ID NO 48
<211> LENGTH: 9
<212> TYPE: PRT
<213> ORGANISM: Homo sapiens, other or unknown

<400> SEQUENCE: 48

Ala Arg Thr Phe Arg Arg Glu Lys Pro
1               5

<210> SEQ ID NO 49
<211> LENGTH: 9
<212> TYPE: PRT
<213> ORGANISM: Homo sapiens, other or unknown

<400> SEQUENCE: 49

Pro Pro Glu Leu Tyr Phe Val Lys Val
1               5

<210> SEQ ID NO 50
<211> LENGTH: 9
<212> TYPE: PRT
<213> ORGANISM: Homo sapiens, other or unknown

<400> SEQUENCE: 50

Glu Leu Tyr Phe Val Lys Val Asp Val
1               5

<210> SEQ ID NO 51
<211> LENGTH: 9
<212> TYPE: PRT
<213> ORGANISM: Homo sapiens, other or unknown

<400> SEQUENCE: 51

Phe Val Lys Val Asp Val Thr Gly Ala
1               5

<210> SEQ ID NO 52
<211> LENGTH: 9
<212> TYPE: PRT
<213> ORGANISM: Homo sapiens, other or unknown

<400> SEQUENCE: 52

Ile Pro Gln Asp Arg Leu Thr Glu Val
1               5

<210> SEQ ID NO 53
<211> LENGTH: 9
<212> TYPE: PRT
<213> ORGANISM: Homo sapiens, other or unknown

<400> SEQUENCE: 53

Asp Arg Leu Thr Glu Val Ile Ala Ser
1               5

<210> SEQ ID NO 54
<211> LENGTH: 9
<212> TYPE: PRT
<213> ORGANISM: Homo sapiens, other or unknown

<400> SEQUENCE: 54

Arg Leu Thr Glu Val Ile Ala Ser Ile
1               5

<210> SEQ ID NO 55
<211> LENGTH: 10
<212> TYPE: PRT
<213> ORGANISM: Homo sapiens, other or unknown

<400> SEQUENCE: 55

Ile Pro Gln Gly Ser Ile Leu Ser Thr Leu
1               5                   10

<210> SEQ ID NO 56
<211> LENGTH: 9
<212> TYPE: PRT
<213> ORGANISM: Homo sapiens, other or unknown

<400> SEQUENCE: 56

Ile Leu Ser Thr Leu Leu Cys Ser Leu
1               5

<210> SEQ ID NO 57
<211> LENGTH: 9
<212> TYPE: PRT
<213> ORGANISM: Homo sapiens, other or unknown

<400> SEQUENCE: 57

Leu Leu Arg Leu Val Asp Asp Phe Leu
1               5

<210> SEQ ID NO 58
<211> LENGTH: 9
<212> TYPE: PRT
<213> ORGANISM: Homo sapiens, other or unknown

<400> SEQUENCE: 58

Arg Leu Val Asp Asp Phe Leu Leu Val
1               5

<210> SEQ ID NO 59
<211> LENGTH: 9
<212> TYPE: PRT
<213> ORGANISM: Homo sapiens, other or unknown

<400> SEQUENCE: 59

```
Val Pro Glu Tyr Gly Cys Val Val Asn
1               5
```

<210> SEQ ID NO 60
<211> LENGTH: 10
<212> TYPE: PRT
<213> ORGANISM: Homo sapiens, other or unknown

<400> SEQUENCE: 60

```
Val Pro Glu Tyr Gly Cys Val Val Asn Leu
1               5                   10
```

<210> SEQ ID NO 61
<211> LENGTH: 9
<212> TYPE: PRT
<213> ORGANISM: Homo sapiens, other or unknown

<400> SEQUENCE: 61

```
Thr Leu Val Arg Gly Val Pro Glu Tyr
1               5
```

<210> SEQ ID NO 62
<211> LENGTH: 9
<212> TYPE: PRT
<213> ORGANISM: Homo sapiens, other or unknown

<400> SEQUENCE: 62

```
Phe Leu Arg Thr Leu Val Arg Gly Val
1               5
```

<210> SEQ ID NO 63
<211> LENGTH: 9
<212> TYPE: PRT
<213> ORGANISM: Homo sapiens, other or unknown

<400> SEQUENCE: 63

```
Gly Val Pro Glu Tyr Gly Cys Val Val
1               5
```

<210> SEQ ID NO 64
<211> LENGTH: 9
<212> TYPE: PRT
<213> ORGANISM: Homo sapiens, other or unknown

<400> SEQUENCE: 64

```
Val Val Asn Leu Arg Lys Thr Val Val
1               5
```

<210> SEQ ID NO 65
<211> LENGTH: 9
<212> TYPE: PRT
<213> ORGANISM: Homo sapiens, other or unknown

<400> SEQUENCE: 65

```
Gly Leu Phe Pro Trp Cys Gly Leu Leu
1               5
```

<210> SEQ ID NO 66
<211> LENGTH: 9
<212> TYPE: PRT
<213> ORGANISM: Homo sapiens, other or unknown

<400> SEQUENCE: 66

```
Tyr Ala Glu Thr Lys His Phe Leu Tyr
1               5
```

<210> SEQ ID NO 67
<211> LENGTH: 9
<212> TYPE: PRT
<213> ORGANISM: Homo sapiens, other or unknown

<400> SEQUENCE: 67

Ile Ser Asp Thr Ala Ser Leu Cys Tyr
1               5

<210> SEQ ID NO 68
<211> LENGTH: 9
<212> TYPE: PRT
<213> ORGANISM: Homo sapiens, other or unknown

<400> SEQUENCE: 68

Asp Thr Asp Pro Arg Arg Leu Val Gln
1               5

<210> SEQ ID NO 69
<211> LENGTH: 9
<212> TYPE: PRT
<213> ORGANISM: Homo sapiens, other or unknown

<400> SEQUENCE: 69

Ala Gln Asp Pro Pro Glu Leu Tyr
1               5

<210> SEQ ID NO 70
<211> LENGTH: 9
<212> TYPE: PRT
<213> ORGANISM: Homo sapiens, other or unknown

<400> SEQUENCE: 70

Leu Thr Asp Leu Gln Pro Tyr Met Arg
1               5

<210> SEQ ID NO 71
<211> LENGTH: 9
<212> TYPE: PRT
<213> ORGANISM: Homo sapiens, other or unknown

<400> SEQUENCE: 71

Gln Ser Asp Tyr Ser Ser Tyr Ala Arg
1               5

<210> SEQ ID NO 72
<211> LENGTH: 9
<212> TYPE: PRT
<213> ORGANISM: Homo sapiens, other or unknown

<400> SEQUENCE: 72

Leu Leu Ala Arg Cys Ala Leu Phe Val
1               5

<210> SEQ ID NO 73
<211> LENGTH: 9
<212> TYPE: PRT
<213> ORGANISM: Homo sapiens, other or unknown

<400> SEQUENCE: 73

Trp Leu Cys His Gln Ala Phe Leu Leu
1               5

```
<210> SEQ ID NO 74
<211> LENGTH: 9
<212> TYPE: PRT
<213> ORGANISM: Homo sapiens, other or unknown

<400> SEQUENCE: 74

Leu Gln Leu Pro Phe His Gln Gln Val
1               5

<210> SEQ ID NO 75
<211> LENGTH: 9
<212> TYPE: PRT
<213> ORGANISM: Homo sapiens, other or unknown

<400> SEQUENCE: 75

Arg Leu Gly Pro Gln Gly Trp Arg Leu
1               5

<210> SEQ ID NO 76
<211> LENGTH: 9
<212> TYPE: PRT
<213> ORGANISM: Homo sapiens, other or unknown

<400> SEQUENCE: 76

Ser Leu Gln Glu Leu Thr Trp Lys Met
1               5

<210> SEQ ID NO 77
<211> LENGTH: 9
<212> TYPE: PRT
<213> ORGANISM: Homo sapiens, other or unknown

<400> SEQUENCE: 77

Asn Val Leu Ala Phe Gly Phe Ala Leu
1               5

<210> SEQ ID NO 78
<211> LENGTH: 9
<212> TYPE: PRT
<213> ORGANISM: Homo sapiens, other or unknown

<400> SEQUENCE: 78

Val Leu Leu Lys Thr His Cys Pro Leu
1               5

<210> SEQ ID NO 79
<211> LENGTH: 9
<212> TYPE: PRT
<213> ORGANISM: Homo sapiens, other or unknown

<400> SEQUENCE: 79

Phe Leu Leu Val Thr Pro His Leu Thr
1               5

<210> SEQ ID NO 80
<211> LENGTH: 9
<212> TYPE: PRT
<213> ORGANISM: Homo sapiens, other or unknown

<400> SEQUENCE: 80

Thr Leu Thr Asp Leu Gln Pro Tyr Met
1               5

<210> SEQ ID NO 81
<211> LENGTH: 9
```

```
<212> TYPE: PRT
<213> ORGANISM: Homo sapiens, other or unknown

<400> SEQUENCE: 81

Phe Leu Asp Leu Gln Val Asn Ser Leu
1               5

<210> SEQ ID NO 82
<211> LENGTH: 9
<212> TYPE: PRT
<213> ORGANISM: Homo sapiens, other or unknown

<400> SEQUENCE: 82

Ser Leu Asn Glu Ala Ser Ser Gly Leu
1               5

<210> SEQ ID NO 83
<211> LENGTH: 9
<212> TYPE: PRT
<213> ORGANISM: Homo sapiens, other or unknown

<400> SEQUENCE: 83

Leu Leu Gly Ala Ser Val Leu Gly Leu
1               5

<210> SEQ ID NO 84
<211> LENGTH: 9
<212> TYPE: PRT
<213> ORGANISM: Homo sapiens, other or unknown

<400> SEQUENCE: 84

Val Leu Ala Phe Gly Phe Ala Leu Leu
1               5

<210> SEQ ID NO 85
<211> LENGTH: 9
<212> TYPE: PRT
<213> ORGANISM: Homo sapiens, other or unknown

<400> SEQUENCE: 85

Leu Gln Pro Tyr Met Arg Gln Phe Val
1               5

<210> SEQ ID NO 86
<211> LENGTH: 9
<212> TYPE: PRT
<213> ORGANISM: Homo sapiens, other or unknown

<400> SEQUENCE: 86

Arg Leu Pro Gln Arg Tyr Trp Gln Met
1               5

<210> SEQ ID NO 87
<211> LENGTH: 9
<212> TYPE: PRT
<213> ORGANISM: Homo sapiens, other or unknown

<400> SEQUENCE: 87

Arg Gln His Ser Ser Pro Trp Gln Val
1               5

<210> SEQ ID NO 88
<211> LENGTH: 9
<212> TYPE: PRT
<213> ORGANISM: Homo sapiens, other or unknown
```

<400> SEQUENCE: 88

Tyr Leu Pro Asn Thr Val Thr Asp Ala
1               5

<210> SEQ ID NO 89
<211> LENGTH: 9
<212> TYPE: PRT
<213> ORGANISM: Homo sapiens, other or unknown

<400> SEQUENCE: 89

Asn Met Arg Arg Lys Leu Phe Gly Val
1               5

<210> SEQ ID NO 90
<211> LENGTH: 9
<212> TYPE: PRT
<213> ORGANISM: Homo sapiens, other or unknown

<400> SEQUENCE: 90

Arg Leu Thr Ser Arg Val Lys Ala Leu
1               5

<210> SEQ ID NO 91
<211> LENGTH: 9
<212> TYPE: PRT
<213> ORGANISM: Homo sapiens, other or unknown

<400> SEQUENCE: 91

Leu Leu Gln Ala Tyr Arg Phe His Ala
1               5

<210> SEQ ID NO 92
<211> LENGTH: 9
<212> TYPE: PRT
<213> ORGANISM: Homo sapiens, other or unknown

<400> SEQUENCE: 92

Leu Leu Asp Thr Arg Thr Leu Glu Val
1               5

<210> SEQ ID NO 93
<211> LENGTH: 9
<212> TYPE: PRT
<213> ORGANISM: Homo sapiens, other or unknown

<400> SEQUENCE: 93

Tyr Met Arg Gln Phe Val Ala His Leu
1               5

<210> SEQ ID NO 94
<211> LENGTH: 9
<212> TYPE: PRT
<213> ORGANISM: Homo sapiens, other or unknown

<400> SEQUENCE: 94

Cys Leu Val Cys Val Pro Trp Asp Ala
1               5

<210> SEQ ID NO 95
<211> LENGTH: 9
<212> TYPE: PRT
<213> ORGANISM: Homo sapiens, other or unknown

<400> SEQUENCE: 95

```
Leu Leu Ser Ser Leu Arg Pro Ser Leu
1               5

<210> SEQ ID NO 96
<211> LENGTH: 9
<212> TYPE: PRT
<213> ORGANISM: Homo sapiens, other or unknown

<400> SEQUENCE: 96

Phe Met Cys His His Ala Val Arg Ile
1               5

<210> SEQ ID NO 97
<211> LENGTH: 9
<212> TYPE: PRT
<213> ORGANISM: Homo sapiens, other or unknown

<400> SEQUENCE: 97

Leu Gln Val Asn Ser Leu Gln Thr Val
1               5

<210> SEQ ID NO 98
<211> LENGTH: 9
<212> TYPE: PRT
<213> ORGANISM: Homo sapiens, other or unknown

<400> SEQUENCE: 98

Leu Val Ala Gln Cys Leu Val Cys Val
1               5

<210> SEQ ID NO 99
<211> LENGTH: 9
<212> TYPE: PRT
<213> ORGANISM: Homo sapiens, other or unknown

<400> SEQUENCE: 99

Cys Leu Lys Glu Leu Val Ala Arg Val
1               5

<210> SEQ ID NO 100
<211> LENGTH: 9
<212> TYPE: PRT
<213> ORGANISM: Homo sapiens, other or unknown

<400> SEQUENCE: 100

Phe Leu Arg Asn Thr Lys Lys Phe Ile
1               5

<210> SEQ ID NO 101
<211> LENGTH: 9
<212> TYPE: PRT
<213> ORGANISM: Homo sapiens, other or unknown

<400> SEQUENCE: 101

Ala Leu Pro Ser Asp Phe Lys Thr Ile
1               5

<210> SEQ ID NO 102
<211> LENGTH: 9
<212> TYPE: PRT
<213> ORGANISM: Homo sapiens, other or unknown

<400> SEQUENCE: 102

Val Leu Val His Leu Leu Ala Arg Cys
```

1               5

<210> SEQ ID NO 103
<211> LENGTH: 9
<212> TYPE: PRT
<213> ORGANISM: Homo sapiens, other or unknown

<400> SEQUENCE: 103

Val Gln Ser Asp Tyr Ser Ser Tyr Ala
1               5

<210> SEQ ID NO 104
<211> LENGTH: 9
<212> TYPE: PRT
<213> ORGANISM: Homo sapiens, other or unknown

<400> SEQUENCE: 104

Ser Val Trp Ser Lys Leu Gln Ser Ile
1               5

<210> SEQ ID NO 105
<211> LENGTH: 9
<212> TYPE: PRT
<213> ORGANISM: Homo sapiens, other or unknown

<400> SEQUENCE: 105

Lys Leu Pro Gly Thr Thr Leu Thr Ala
1               5

<210> SEQ ID NO 106
<211> LENGTH: 9
<212> TYPE: PRT
<213> ORGANISM: Homo sapiens, other or unknown

<400> SEQUENCE: 106

Gln Leu Ser Arg Lys Leu Pro Gly Thr
1               5

<210> SEQ ID NO 107
<211> LENGTH: 9
<212> TYPE: PRT
<213> ORGANISM: Homo sapiens, other or unknown

<400> SEQUENCE: 107

Gly Leu Leu Leu Asp Thr Arg Thr Leu
1               5

<210> SEQ ID NO 108
<211> LENGTH: 9
<212> TYPE: PRT
<213> ORGANISM: Homo sapiens, other or unknown

<400> SEQUENCE: 108

Trp Met Pro Gly Thr Pro Arg Arg Leu
1               5

<210> SEQ ID NO 109
<211> LENGTH: 9
<212> TYPE: PRT
<213> ORGANISM: Homo sapiens, other or unknown

<400> SEQUENCE: 109

Ser Leu Thr Gly Ala Arg Arg Leu Val
1               5

<210> SEQ ID NO 110
<211> LENGTH: 9
<212> TYPE: PRT
<213> ORGANISM: Homo sapiens, other or unknown

<400> SEQUENCE: 110

Val Val Ile Glu Gln Ser Ser Ser Leu
1               5

<210> SEQ ID NO 111
<211> LENGTH: 9
<212> TYPE: PRT
<213> ORGANISM: Homo sapiens, other or unknown

<400> SEQUENCE: 111

Leu Pro Ser Glu Ala Val Gln Trp Leu
1               5

<210> SEQ ID NO 112
<211> LENGTH: 9
<212> TYPE: PRT
<213> ORGANISM: Homo sapiens, other or unknown

<400> SEQUENCE: 112

Gln Ala Tyr Arg Phe His Ala Cys Val
1               5

<210> SEQ ID NO 113
<211> LENGTH: 9
<212> TYPE: PRT
<213> ORGANISM: Homo sapiens, other or unknown

<400> SEQUENCE: 113

Gly Leu Phe Asp Val Phe Leu Arg Phe
1               5

<210> SEQ ID NO 114
<211> LENGTH: 9
<212> TYPE: PRT
<213> ORGANISM: Homo sapiens, other or unknown

<400> SEQUENCE: 114

Lys Leu Phe Gly Val Leu Arg Leu Lys
1               5

<210> SEQ ID NO 115
<211> LENGTH: 9
<212> TYPE: PRT
<213> ORGANISM: Homo sapiens, other or unknown

<400> SEQUENCE: 115

Arg Leu Arg Glu Glu Ile Leu Ala Lys
1               5

<210> SEQ ID NO 116
<211> LENGTH: 9
<212> TYPE: PRT
<213> ORGANISM: Homo sapiens, other or unknown

<400> SEQUENCE: 116

Gly Leu Pro Ala Pro Gly Ala Arg Arg
1               5

<210> SEQ ID NO 117

```
<211> LENGTH: 9
<212> TYPE: PRT
<213> ORGANISM: Homo sapiens, other or unknown

<400> SEQUENCE: 117

Lys Leu Thr Arg His Arg Val Thr Tyr
1               5

<210> SEQ ID NO 118
<211> LENGTH: 9
<212> TYPE: PRT
<213> ORGANISM: Homo sapiens, other or unknown

<400> SEQUENCE: 118

Val Leu Pro Leu Ala Thr Phe Val Arg
1               5

<210> SEQ ID NO 119
<211> LENGTH: 9
<212> TYPE: PRT
<213> ORGANISM: Homo sapiens, other or unknown

<400> SEQUENCE: 119

Glu Leu Val Ala Arg Val Leu Gln Arg
1               5

<210> SEQ ID NO 120
<211> LENGTH: 9
<212> TYPE: PRT
<213> ORGANISM: Homo sapiens, other or unknown

<400> SEQUENCE: 120

Asp Pro Arg Arg Leu Val Gln Leu Leu
1               5

<210> SEQ ID NO 121
<211> LENGTH: 9
<212> TYPE: PRT
<213> ORGANISM: Homo sapiens, other or unknown

<400> SEQUENCE: 121

Phe Val Arg Ala Cys Leu Arg Arg Leu
1               5

<210> SEQ ID NO 122
<211> LENGTH: 9
<212> TYPE: PRT
<213> ORGANISM: Homo sapiens, other or unknown

<400> SEQUENCE: 122

Ser Val Arg Glu Ala Gly Val Pro Leu
1               5

<210> SEQ ID NO 123
<211> LENGTH: 9
<212> TYPE: PRT
<213> ORGANISM: Homo sapiens, other or unknown

<400> SEQUENCE: 123

Ala Gly Arg Asn Met Arg Arg Lys Leu
1               5

<210> SEQ ID NO 124
<211> LENGTH: 9
<212> TYPE: PRT
```

```
<213> ORGANISM: Homo sapiens, other or unknown

<400> SEQUENCE: 124

Leu Ala Arg Cys Ala Leu Phe Val Leu
1               5

<210> SEQ ID NO 125
<211> LENGTH: 9
<212> TYPE: PRT
<213> ORGANISM: Homo sapiens, other or unknown

<400> SEQUENCE: 125

Arg Pro Ala Glu Glu Ala Thr Ser Leu
1               5

<210> SEQ ID NO 126
<211> LENGTH: 9
<212> TYPE: PRT
<213> ORGANISM: Homo sapiens, other or unknown

<400> SEQUENCE: 126

Leu Pro Ser Asp Phe Lys Thr Ile Leu
1               5

<210> SEQ ID NO 127
<211> LENGTH: 9
<212> TYPE: PRT
<213> ORGANISM: Homo sapiens, other or unknown

<400> SEQUENCE: 127

Leu Pro Gly Thr Thr Leu Thr Ala Leu
1               5

<210> SEQ ID NO 128
<211> LENGTH: 9
<212> TYPE: PRT
<213> ORGANISM: Homo sapiens, other or unknown

<400> SEQUENCE: 128

Arg Pro Ser Phe Leu Leu Ser Ser Leu
1               5

<210> SEQ ID NO 129
<211> LENGTH: 9
<212> TYPE: PRT
<213> ORGANISM: Homo sapiens, other or unknown

<400> SEQUENCE: 129

Leu Pro Asn Thr Val Thr Asp Ala Leu
1               5

<210> SEQ ID NO 130
<211> LENGTH: 9
<212> TYPE: PRT
<213> ORGANISM: Homo sapiens, other or unknown

<400> SEQUENCE: 130

Arg Cys Arg Ala Val Arg Ser Leu Leu
1               5

<210> SEQ ID NO 131
<211> LENGTH: 9
<212> TYPE: PRT
<213> ORGANISM: Homo sapiens, other or unknown
```

```
<400> SEQUENCE: 131

Met Pro Arg Ala Pro Arg Cys Arg Ala
1               5

<210> SEQ ID NO 132
<211> LENGTH: 9
<212> TYPE: PRT
<213> ORGANISM: Homo sapiens, other or unknown

<400> SEQUENCE: 132

Gly Ile Arg Arg Asp Gly Leu Leu Leu
1               5

<210> SEQ ID NO 133
<211> LENGTH: 9
<212> TYPE: PRT
<213> ORGANISM: Homo sapiens, other or unknown

<400> SEQUENCE: 133

Val Leu Arg Leu Lys Cys His Ser Leu
1               5

<210> SEQ ID NO 134
<211> LENGTH: 9
<212> TYPE: PRT
<213> ORGANISM: Homo sapiens, other or unknown

<400> SEQUENCE: 134

Ser Leu Arg Thr Ala Gln Thr Gln Leu
1               5

<210> SEQ ID NO 135
<211> LENGTH: 9
<212> TYPE: PRT
<213> ORGANISM: Homo sapiens, other or unknown

<400> SEQUENCE: 135

Gln Met Arg Pro Leu Phe Leu Glu Leu
1               5

<210> SEQ ID NO 136
<211> LENGTH: 9
<212> TYPE: PRT
<213> ORGANISM: Homo sapiens, other or unknown

<400> SEQUENCE: 136

Phe Val Gln Met Pro Ala His Gly Leu
1               5

<210> SEQ ID NO 137
<211> LENGTH: 9
<212> TYPE: PRT
<213> ORGANISM: Homo sapiens, other or unknown

<400> SEQUENCE: 137

His Ala Ser Gly Pro Arg Arg Arg Leu
1               5

<210> SEQ ID NO 138
<211> LENGTH: 9
<212> TYPE: PRT
<213> ORGANISM: Homo sapiens, other or unknown

<400> SEQUENCE: 138
```

```
Arg Val Ile Ser Asp Thr Ala Ser Leu
1               5

<210> SEQ ID NO 139
<211> LENGTH: 9
<212> TYPE: PRT
<213> ORGANISM: Homo sapiens, other or unknown

<400> SEQUENCE: 139

Cys Val Pro Ala Ala Glu His Arg Leu
1               5

<210> SEQ ID NO 140
<211> LENGTH: 9
<212> TYPE: PRT
<213> ORGANISM: Homo sapiens, other or unknown

<400> SEQUENCE: 140

Arg Val Lys Ala Leu Phe Ser Val Leu
1               5

<210> SEQ ID NO 141
<211> LENGTH: 9
<212> TYPE: PRT
<213> ORGANISM: Homo sapiens, other or unknown

<400> SEQUENCE: 141

Leu Val Ala Arg Val Leu Gln Arg Leu
1               5

<210> SEQ ID NO 142
<211> LENGTH: 9
<212> TYPE: PRT
<213> ORGANISM: Homo sapiens, other or unknown

<400> SEQUENCE: 142

Phe Ala Gly Ile Arg Arg Asp Gly Leu
1               5

<210> SEQ ID NO 143
<211> LENGTH: 9
<212> TYPE: PRT
<213> ORGANISM: Homo sapiens, other or unknown

<400> SEQUENCE: 143

His Ala Gln Cys Pro Tyr Gly Val Leu
1               5

<210> SEQ ID NO 144
<211> LENGTH: 9
<212> TYPE: PRT
<213> ORGANISM: Homo sapiens, other or unknown

<400> SEQUENCE: 144

Arg Ala Gln Asp Pro Pro Glu Leu
1               5

<210> SEQ ID NO 145
<211> LENGTH: 9
<212> TYPE: PRT
<213> ORGANISM: Homo sapiens, other or unknown

<400> SEQUENCE: 145

Ala Tyr Arg Phe His Ala Cys Val Leu
1               5
```

<210> SEQ ID NO 146
<211> LENGTH: 9
<212> TYPE: PRT
<213> ORGANISM: Homo sapiens, other or unknown

<400> SEQUENCE: 146

His Ala Lys Leu Ser Leu Gln Glu Leu
1               5

<210> SEQ ID NO 147
<211> LENGTH: 9
<212> TYPE: PRT
<213> ORGANISM: Homo sapiens, other or unknown

<400> SEQUENCE: 147

Gly Ala Lys Gly Ala Ala Gly Pro Leu
1               5

<210> SEQ ID NO 148
<211> LENGTH: 9
<212> TYPE: PRT
<213> ORGANISM: Homo sapiens, other or unknown

<400> SEQUENCE: 148

Thr Ala Ser Leu Cys Tyr Ser Ile Leu
1               5

<210> SEQ ID NO 149
<211> LENGTH: 9
<212> TYPE: PRT
<213> ORGANISM: Homo sapiens, other or unknown

<400> SEQUENCE: 149

Ala Pro Arg Cys Arg Ala Val Arg Ser
1               5

<210> SEQ ID NO 150
<211> LENGTH: 9
<212> TYPE: PRT
<213> ORGANISM: Homo sapiens, other or unknown

<400> SEQUENCE: 150

Gly Ala Arg Arg Leu Val Glu Thr Ile
1               5

<210> SEQ ID NO 151
<211> LENGTH: 9
<212> TYPE: PRT
<213> ORGANISM: Homo sapiens, other or unknown

<400> SEQUENCE: 151

Ala Gln Cys Pro Tyr Gly Val Leu Leu
1               5

<210> SEQ ID NO 152
<211> LENGTH: 9
<212> TYPE: PRT
<213> ORGANISM: Homo sapiens, other or unknown

<400> SEQUENCE: 152

His Ala Lys Thr Phe Leu Arg Thr Leu
1               5

```
<210> SEQ ID NO 153
<211> LENGTH: 9
<212> TYPE: PRT
<213> ORGANISM: Homo sapiens, other or unknown

<400> SEQUENCE: 153

Glu Ala Thr Ser Leu Glu Gly Ala Leu
1               5

<210> SEQ ID NO 154
<211> LENGTH: 9
<212> TYPE: PRT
<213> ORGANISM: Homo sapiens, other or unknown

<400> SEQUENCE: 154

Lys Ala Lys Asn Ala Gly Met Ser Leu
1               5

<210> SEQ ID NO 155
<211> LENGTH: 9
<212> TYPE: PRT
<213> ORGANISM: Homo sapiens, other or unknown

<400> SEQUENCE: 155

Ala Gln Thr Gln Leu Ser Arg Lys Leu
1               5

<210> SEQ ID NO 156
<211> LENGTH: 9
<212> TYPE: PRT
<213> ORGANISM: Homo sapiens, other or unknown

<400> SEQUENCE: 156

Ala Gly Ile Arg Arg Asp Gly Leu Leu
1               5

<210> SEQ ID NO 157
<211> LENGTH: 9
<212> TYPE: PRT
<213> ORGANISM: Homo sapiens, other or unknown

<400> SEQUENCE: 157

Ile Leu Lys Ala Lys Asn Ala Gly Met
1               5

<210> SEQ ID NO 158
<211> LENGTH: 9
<212> TYPE: PRT
<213> ORGANISM: Homo sapiens, other or unknown

<400> SEQUENCE: 158

Asp Pro Arg Arg Leu Val Gln Leu Leu
1               5

<210> SEQ ID NO 159
<211> LENGTH: 9
<212> TYPE: PRT
<213> ORGANISM: Homo sapiens, other or unknown

<400> SEQUENCE: 159

Gly Ala Arg Arg Arg Gly Gly Ser Ala
1               5

<210> SEQ ID NO 160
<211> LENGTH: 9
```

```
<212> TYPE: PRT
<213> ORGANISM: Homo sapiens, other or unknown

<400> SEQUENCE: 160

Glu His Arg Leu Arg Glu Glu Ile Leu
1               5

<210> SEQ ID NO 161
<211> LENGTH: 9
<212> TYPE: PRT
<213> ORGANISM: Homo sapiens, other or unknown

<400> SEQUENCE: 161

Cys Ala Arg Glu Lys Pro Gln Gly Ser
1               5

<210> SEQ ID NO 162
<211> LENGTH: 9
<212> TYPE: PRT
<213> ORGANISM: Homo sapiens, other or unknown

<400> SEQUENCE: 162

Leu Thr Arg His Arg Val Thr Tyr Val
1               5

<210> SEQ ID NO 163
<211> LENGTH: 9
<212> TYPE: PRT
<213> ORGANISM: Homo sapiens, other or unknown

<400> SEQUENCE: 163

Arg Arg Phe Leu Arg Asn Thr Lys Lys
1               5

<210> SEQ ID NO 164
<211> LENGTH: 9
<212> TYPE: PRT
<213> ORGANISM: Homo sapiens, other or unknown

<400> SEQUENCE: 164

Arg Arg Asp Gly Leu Leu Leu Arg Leu
1               5

<210> SEQ ID NO 165
<211> LENGTH: 9
<212> TYPE: PRT
<213> ORGANISM: Homo sapiens, other or unknown

<400> SEQUENCE: 165

Arg Arg Glu Lys Arg Ala Glu Arg Leu
1               5

<210> SEQ ID NO 166
<211> LENGTH: 9
<212> TYPE: PRT
<213> ORGANISM: Homo sapiens, other or unknown

<400> SEQUENCE: 166

Arg Arg Leu Val Glu Thr Ile Phe Leu
1               5

<210> SEQ ID NO 167
<211> LENGTH: 9
<212> TYPE: PRT
<213> ORGANISM: Homo sapiens, other or unknown
```

-continued

```
<400> SEQUENCE: 167

Leu Arg Phe Met Cys His His Ala Val
1               5

<210> SEQ ID NO 168
<211> LENGTH: 9
<212> TYPE: PRT
<213> ORGANISM: Homo sapiens, other or unknown

<400> SEQUENCE: 168

Arg Arg Tyr Ala Val Val Gln Lys Ala
1               5

<210> SEQ ID NO 169
<211> LENGTH: 9
<212> TYPE: PRT
<213> ORGANISM: Homo sapiens, other or unknown

<400> SEQUENCE: 169

Lys Arg Ala Glu Arg Leu Thr Ser Arg
1               5

<210> SEQ ID NO 170
<211> LENGTH: 9
<212> TYPE: PRT
<213> ORGANISM: Homo sapiens, other or unknown

<400> SEQUENCE: 170

Arg Arg Lys Leu Phe Gly Val Leu Arg
1               5

<210> SEQ ID NO 171
<211> LENGTH: 9
<212> TYPE: PRT
<213> ORGANISM: Homo sapiens, other or unknown

<400> SEQUENCE: 171

Arg Arg Arg Gly Gly Ser Ala Ser Arg
1               5

<210> SEQ ID NO 172
<211> LENGTH: 9
<212> TYPE: PRT
<213> ORGANISM: Homo sapiens, other or unknown

<400> SEQUENCE: 172

Arg Arg Leu Pro Arg Leu Pro Gln Arg
1               5

<210> SEQ ID NO 173
<211> LENGTH: 9
<212> TYPE: PRT
<213> ORGANISM: Homo sapiens, other or unknown

<400> SEQUENCE: 173

Arg Arg Leu Gly Pro Gln Gly Trp Arg
1               5

<210> SEQ ID NO 174
<211> LENGTH: 9
<212> TYPE: PRT
<213> ORGANISM: Homo sapiens, other or unknown

<400> SEQUENCE: 174
```

```
Leu Arg Gly Ser Gly Ala Trp Gly Leu
1               5

<210> SEQ ID NO 175
<211> LENGTH: 9
<212> TYPE: PRT
<213> ORGANISM: Homo sapiens, other or unknown

<400> SEQUENCE: 175

His Arg Glu Ala Arg Pro Ala Leu Leu
1               5

<210> SEQ ID NO 176
<211> LENGTH: 9
<212> TYPE: PRT
<213> ORGANISM: Homo sapiens, other or unknown

<400> SEQUENCE: 176

Val Arg Arg Tyr Ala Val Val Gln Lys
1               5

<210> SEQ ID NO 177
<211> LENGTH: 9
<212> TYPE: PRT
<213> ORGANISM: Homo sapiens, other or unknown

<400> SEQUENCE: 177

Ala Arg Thr Ser Ile Arg Ala Ser Leu
1               5

<210> SEQ ID NO 178
<211> LENGTH: 9
<212> TYPE: PRT
<213> ORGANISM: Homo sapiens, other or unknown

<400> SEQUENCE: 178

His Arg Val Thr Tyr Val Pro Leu Leu
1               5

<210> SEQ ID NO 179
<211> LENGTH: 9
<212> TYPE: PRT
<213> ORGANISM: Homo sapiens, other or unknown

<400> SEQUENCE: 179

Leu Arg Ser His Tyr Arg Glu Val Leu
1               5

<210> SEQ ID NO 180
<211> LENGTH: 9
<212> TYPE: PRT
<213> ORGANISM: Homo sapiens, other or unknown

<400> SEQUENCE: 180

Met Arg Pro Leu Phe Leu Glu Leu Leu
1               5

<210> SEQ ID NO 181
<211> LENGTH: 9
<212> TYPE: PRT
<213> ORGANISM: Homo sapiens, other or unknown

<400> SEQUENCE: 181

His Arg Ala Trp Arg Thr Phe Val Leu
```

```
1               5

<210> SEQ ID NO 182
<211> LENGTH: 9
<212> TYPE: PRT
<213> ORGANISM: Homo sapiens, other or unknown

<400> SEQUENCE: 182

Met Arg Arg Lys Leu Phe Gly Val Leu
1               5

<210> SEQ ID NO 183
<211> LENGTH: 9
<212> TYPE: PRT
<213> ORGANISM: Homo sapiens, other or unknown

<400> SEQUENCE: 183

Leu Arg Leu Val Asp Asp Phe Leu Leu
1               5

<210> SEQ ID NO 184
<211> LENGTH: 9
<212> TYPE: PRT
<213> ORGANISM: Homo sapiens, other or unknown

<400> SEQUENCE: 184

Leu Arg Arg Val Gly Asp Asp Val Leu
1               5

<210> SEQ ID NO 185
<211> LENGTH: 9
<212> TYPE: PRT
<213> ORGANISM: Homo sapiens, other or unknown

<400> SEQUENCE: 185

Tyr Arg Lys Ser Val Trp Ser Lys Leu
1               5

<210> SEQ ID NO 186
<211> LENGTH: 9
<212> TYPE: PRT
<213> ORGANISM: Homo sapiens, other or unknown

<400> SEQUENCE: 186

Gln Arg Leu Cys Glu Arg Gly Ala Lys
1               5

<210> SEQ ID NO 187
<211> LENGTH: 9
<212> TYPE: PRT
<213> ORGANISM: Homo sapiens, other or unknown

<400> SEQUENCE: 187

Phe Arg Ala Leu Val Ala Gln Cys Leu
1               5

<210> SEQ ID NO 188
<211> LENGTH: 9
<212> TYPE: PRT
<213> ORGANISM: Homo sapiens, other or unknown

<400> SEQUENCE: 188

Ser Arg Lys Leu Pro Gly Thr Thr Leu
1               5
```

```
<210> SEQ ID NO 189
<211> LENGTH: 9
<212> TYPE: PRT
<213> ORGANISM: Homo sapiens, other or unknown

<400> SEQUENCE: 189

Leu Arg Arg Leu Val Pro Pro Gly Leu
1               5

<210> SEQ ID NO 190
<211> LENGTH: 9
<212> TYPE: PRT
<213> ORGANISM: Homo sapiens, other or unknown

<400> SEQUENCE: 190

Arg Arg Ser Pro Gly Val Gly Cys Val
1               5

<210> SEQ ID NO 191
<211> LENGTH: 9
<212> TYPE: PRT
<213> ORGANISM: Homo sapiens, other or unknown

<400> SEQUENCE: 191

Arg Arg Val Gly Asp Asp Val Leu Val
1               5

<210> SEQ ID NO 192
<211> LENGTH: 9
<212> TYPE: PRT
<213> ORGANISM: Homo sapiens, other or unknown

<400> SEQUENCE: 192

Val Arg Gly Cys Ala Trp Leu Arg Arg
1               5

<210> SEQ ID NO 193
<211> LENGTH: 9
<212> TYPE: PRT
<213> ORGANISM: Homo sapiens, other or unknown

<400> SEQUENCE: 193

Val Arg Ser Leu Leu Arg Ser His Tyr
1               5

<210> SEQ ID NO 194
<211> LENGTH: 9
<212> TYPE: PRT
<213> ORGANISM: Homo sapiens, other or unknown

<400> SEQUENCE: 194

Ala Arg Thr Phe Arg Arg Glu Lys Arg
1               5

<210> SEQ ID NO 195
<211> LENGTH: 9
<212> TYPE: PRT
<213> ORGANISM: Homo sapiens, other or unknown

<400> SEQUENCE: 195

Ser Arg Ser Leu Pro Leu Pro Lys Arg
1               5

<210> SEQ ID NO 196
```

```
<211> LENGTH: 9
<212> TYPE: PRT
<213> ORGANISM: Homo sapiens, other or unknown

<400> SEQUENCE: 196

Ile Arg Ala Ser Leu Thr Phe Asn Arg
1               5

<210> SEQ ID NO 197
<211> LENGTH: 9
<212> TYPE: PRT
<213> ORGANISM: Homo sapiens, other or unknown

<400> SEQUENCE: 197

Leu Arg Glu Glu Ile Leu Ala Lys Phe
1               5

<210> SEQ ID NO 198
<211> LENGTH: 9
<212> TYPE: PRT
<213> ORGANISM: Homo sapiens, other or unknown

<400> SEQUENCE: 198

Ile Arg Arg Asp Gly Leu Leu Leu Arg
1               5

<210> SEQ ID NO 199
<211> LENGTH: 9
<212> TYPE: PRT
<213> ORGANISM: Homo sapiens, other or unknown

<400> SEQUENCE: 199

Gln Arg Gly Asp Pro Ala Ala Phe Arg
1               5

<210> SEQ ID NO 200
<211> LENGTH: 9
<212> TYPE: PRT
<213> ORGANISM: Homo sapiens, other or unknown

<400> SEQUENCE: 200

Ala Arg Arg Leu Val Glu Thr Ile Phe
1               5

<210> SEQ ID NO 201
<211> LENGTH: 9
<212> TYPE: PRT
<213> ORGANISM: Homo sapiens, other or unknown

<400> SEQUENCE: 201

Leu Arg Pro Ser Leu Thr Gly Ala Arg
1               5

<210> SEQ ID NO 202
<211> LENGTH: 9
<212> TYPE: PRT
<213> ORGANISM: Homo sapiens, other or unknown

<400> SEQUENCE: 202

Leu Arg Leu Lys Cys His Ser Leu Phe
1               5

<210> SEQ ID NO 203
<211> LENGTH: 9
<212> TYPE: PRT
```

-continued

<213> ORGANISM: Homo sapiens, other or unknown

<400> SEQUENCE: 203

Phe Arg Arg Glu Lys Arg Ala Glu Arg
1               5

<210> SEQ ID NO 204
<211> LENGTH: 9
<212> TYPE: PRT
<213> ORGANISM: Homo sapiens, other or unknown

<400> SEQUENCE: 204

Ala Arg Gly Gly Pro Pro Glu Ala Phe
1               5

<210> SEQ ID NO 205
<211> LENGTH: 9
<212> TYPE: PRT
<213> ORGANISM: Homo sapiens, other or unknown

<400> SEQUENCE: 205

Cys Arg Ala Val Arg Ser Leu Leu Arg
1               5

<210> SEQ ID NO 206
<211> LENGTH: 9
<212> TYPE: PRT
<213> ORGANISM: Homo sapiens, other or unknown

<400> SEQUENCE: 206

Gly Arg Thr Arg Gly Pro Ser Asp Arg
1               5

<210> SEQ ID NO 207
<211> LENGTH: 9
<212> TYPE: PRT
<213> ORGANISM: Homo sapiens, other or unknown

<400> SEQUENCE: 207

Arg Arg Arg Leu Gly Cys Glu Arg Ala
1               5

<210> SEQ ID NO 208
<211> LENGTH: 9
<212> TYPE: PRT
<213> ORGANISM: Homo sapiens, other or unknown

<400> SEQUENCE: 208

Leu Arg Glu Leu Ser Glu Ala Glu Val
1               5

<210> SEQ ID NO 209
<211> LENGTH: 9
<212> TYPE: PRT
<213> ORGANISM: Homo sapiens, other or unknown

<400> SEQUENCE: 209

Ala Arg Cys Ala Leu Phe Val Leu Val
1               5

<210> SEQ ID NO 210
<211> LENGTH: 9
<212> TYPE: PRT
<213> ORGANISM: Homo sapiens, other or unknown -continued

```
<400> SEQUENCE: 210

Arg Pro Pro Pro Ala Ala Pro Ser Phe
1               5

<210> SEQ ID NO 211
<211> LENGTH: 9
<212> TYPE: PRT
<213> ORGANISM: Homo sapiens, other or unknown

<400> SEQUENCE: 211

Leu Pro Arg Leu Pro Gln Arg Tyr Trp
1               5

<210> SEQ ID NO 212
<211> LENGTH: 9
<212> TYPE: PRT
<213> ORGANISM: Homo sapiens, other or unknown

<400> SEQUENCE: 212

Leu Ala Lys Phe Leu His Trp Leu Met
1               5

<210> SEQ ID NO 213
<211> LENGTH: 9
<212> TYPE: PRT
<213> ORGANISM: Homo sapiens, other or unknown

<400> SEQUENCE: 213

Gly Ser Arg His Asn Glu Arg Arg Phe
1               5

<210> SEQ ID NO 214
<211> LENGTH: 9
<212> TYPE: PRT
<213> ORGANISM: Homo sapiens, other or unknown

<400> SEQUENCE: 214

Lys Ala Leu Phe Ser Val Leu Asn Tyr
1               5

<210> SEQ ID NO 215
<211> LENGTH: 9
<212> TYPE: PRT
<213> ORGANISM: Homo sapiens, other or unknown

<400> SEQUENCE: 215

Ser Pro Leu Arg Asp Ala Val Val Ile
1               5

<210> SEQ ID NO 216
<211> LENGTH: 9
<212> TYPE: PRT
<213> ORGANISM: Homo sapiens, other or unknown

<400> SEQUENCE: 216

Met Pro Ala His Gly Leu Phe Pro Trp
1               5

<210> SEQ ID NO 217
<211> LENGTH: 9
<212> TYPE: PRT
<213> ORGANISM: Homo sapiens, other or unknown

<400> SEQUENCE: 217
```

Ala Glu Val Arg Gln His Arg Glu Ala
1               5

<210> SEQ ID NO 218
<211> LENGTH: 9
<212> TYPE: PRT
<213> ORGANISM: Homo sapiens, other or unknown

<400> SEQUENCE: 218

Arg Glu Ala Gly Val Pro Leu Gly Leu
1               5

<210> SEQ ID NO 219
<211> LENGTH: 9
<212> TYPE: PRT
<213> ORGANISM: Homo sapiens, other or unknown

<400> SEQUENCE: 219

Glu Glu Ala Thr Ser Leu Glu Gly Ala
1               5

<210> SEQ ID NO 220
<211> LENGTH: 9
<212> TYPE: PRT
<213> ORGANISM: Homo sapiens, other or unknown

<400> SEQUENCE: 220

Leu Glu Ala Ala Ala Asn Pro Ala Leu
1               5

<210> SEQ ID NO 221
<211> LENGTH: 9
<212> TYPE: PRT
<213> ORGANISM: Homo sapiens, other or unknown

<400> SEQUENCE: 221

Gln Glu Thr Ser Pro Leu Arg Asp Ala
1               5

<210> SEQ ID NO 222
<211> LENGTH: 9
<212> TYPE: PRT
<213> ORGANISM: Homo sapiens, other or unknown

<400> SEQUENCE: 222

Arg Glu Val Leu Pro Leu Ala Thr Phe
1               5

<210> SEQ ID NO 223
<211> LENGTH: 9
<212> TYPE: PRT
<213> ORGANISM: Homo sapiens, other or unknown

<400> SEQUENCE: 223

Lys Glu Gln Leu Arg Pro Ser Phe Leu
1               5

<210> SEQ ID NO 224
<211> LENGTH: 9
<212> TYPE: PRT
<213> ORGANISM: Homo sapiens, other or unknown

<400> SEQUENCE: 224

Arg Glu Lys Pro Gln Gly Ser Val Ala
1               5

```
<210> SEQ ID NO 225
<211> LENGTH: 9
<212> TYPE: PRT
<213> ORGANISM: Homo sapiens, other or unknown

<400> SEQUENCE: 225

Leu Glu Val Gln Ser Asp Tyr Ser Ser
1               5

<210> SEQ ID NO 226
<211> LENGTH: 9
<212> TYPE: PRT
<213> ORGANISM: Homo sapiens, other or unknown

<400> SEQUENCE: 226

Arg Glu Ala Arg Pro Ala Leu Leu Thr
1               5

<210> SEQ ID NO 227
<211> LENGTH: 9
<212> TYPE: PRT
<213> ORGANISM: Homo sapiens, other or unknown

<400> SEQUENCE: 227

Glu Glu Asp Thr Asp Pro Arg Arg Leu
1               5

<210> SEQ ID NO 228
<211> LENGTH: 9
<212> TYPE: PRT
<213> ORGANISM: Homo sapiens, other or unknown

<400> SEQUENCE: 228

Cys Glu Arg Gly Ala Lys Asn Val Leu
1               5

<210> SEQ ID NO 229
<211> LENGTH: 9
<212> TYPE: PRT
<213> ORGANISM: Homo sapiens, other or unknown

<400> SEQUENCE: 229

Asp Asp Val Leu Val His Leu Leu Ala
1               5

<210> SEQ ID NO 230
<211> LENGTH: 9
<212> TYPE: PRT
<213> ORGANISM: Homo sapiens, other or unknown

<400> SEQUENCE: 230

Gly Asp Met Glu Asn Lys Leu Phe Ala
1               5

<210> SEQ ID NO 231
<211> LENGTH: 9
<212> TYPE: PRT
<213> ORGANISM: Homo sapiens, other or unknown

<400> SEQUENCE: 231

Tyr Glu Arg Ala Arg Arg Pro Gly Leu
1               5
```